United States Patent
Arce Saez et al.

(10) Patent No.: US 12,311,012 B2
(45) Date of Patent: May 27, 2025

(54) COMPOSITIONS AND METHODS FOR CONTROLLED OVARIAN STIMULATION

(71) Applicant: FERRING B.V., Hoofddorp (NL)

(72) Inventors: Joan-Carles Arce Saez, Copenhagen (DK); Lisbeth Helmgaard, Copenhagen (DK); Bjarke Mirner Klein, Copenhagen (DK); Patrick Heiser, Parsippany, NJ (US)

(73) Assignee: Ferring B.V., Hoofddorp (NL)

( * ) Notice: Subject to any disclaimer, the term of this patent is extended or adjusted under 35 U.S.C. 154(b) by 344 days.

(21) Appl. No.: 17/285,314

(22) PCT Filed: Oct. 17, 2019

(86) PCT No.: PCT/EP2019/078170
§ 371 (c)(1),
(2) Date: Apr. 14, 2021

(87) PCT Pub. No.: WO2020/079127
PCT Pub. Date: Apr. 23, 2020

(65) Prior Publication Data
US 2021/0353717 A1  Nov. 18, 2021

Related U.S. Application Data

(60) Provisional application No. 62/746,812, filed on Oct. 17, 2018.

(30) Foreign Application Priority Data

Oct. 29, 2018 (EP) ..................... 18203167

(51) Int. Cl.
*A61K 38/24* (2006.01)
*A61P 15/08* (2006.01)

(52) U.S. Cl.
CPC .............. *A61K 38/24* (2013.01); *A61P 15/08* (2018.01)

(58) Field of Classification Search
None
See application file for complete search history.

(56) References Cited

U.S. PATENT DOCUMENTS

| | | |
|---|---|---|
| 8,951,967 B2 | 2/2015 | Cottingham et al. |
| 9,546,204 B2 | 1/2017 | Cottingham et al. |
| 9,694,052 B2 | 7/2017 | Arce |
| 9,771,407 B2 | 9/2017 | Cottingham et al. |
| 10,624,953 B2 | 4/2020 | Arce |
| 10,995,128 B2 | 5/2021 | Cottingham et al. |
| 11,291,708 B2 | 4/2022 | Arce |
| 11,744,879 B2 | 9/2023 | Arce Saez |
| 11,952,407 B2 | 4/2024 | Cottingham et al. |
| 2014/0234968 A1 | 8/2014 | Chung et al. |
| 2021/0038694 A1 | 2/2021 | Cottingham |
| 2022/0370567 A1 | 11/2022 | Arce |
| 2024/0024424 A1 | 1/2024 | Arce Saez et al. |
| 2024/0033329 A1 | 2/2024 | Arce |
| 2024/0327487 A1 | 10/2024 | Cottingham et al. |

FOREIGN PATENT DOCUMENTS

| | | |
|---|---|---|
| EP | 1 364 658 A1 | 11/2003 |
| WO | WO-03/022303 A2 | 3/2003 |
| WO | WO-2012/168680 A1 | 12/2012 |
| WO | WO-2016/166288 A1 | 10/2016 |

OTHER PUBLICATIONS

Broer et al., Human Reproduction Update, vol. 20, No. 5 pp. 688-701, 2014 (Year: 2014).*
Scheffer et al., Fertility and Sterility, 72: 1999: 845-851 (Year: 1999).*
de Vet et al., Fertility and Sterility, 77: 2002: 357-362 (Year: 2002).*
Crawford NM and Steiner AZ., Obstet Gynecol Clin North Am. Mar. 2015;42(1):15-25. doi: 10.1016/j.ogc.2014.09.005. Epub Dec. 5, 2014 (Year: 2014).*
Scheffer et al., JBRA Assisted Reproduction 2018;22(3):215-220 doi: 10.5935/1518-0557.20180043 (Year: 2018).*
Andersen et al., "Clinical outcome following stimulation with highly purified hMG or recombinant FSH in patients undergoing IVF: a randomized assessor-blind controlled trial," Human Reproduction, vol. 21, No. 12, pp. 3217-3227, XP055658035 (Dec. 2006).
Cavagna et al., "P-741 Comparison of 225 IU and 300 IU Follitropin-A in a Fixed-Dose Regimen for Controlled Ovarian Stimulation in Women Aged 35 Years or Older," Fertility and Sterility, vol. 86, Supplement 2 (2006), p. S408, doi:10.1016/j.fertnstert.2006.07.1127.
Chang et al., "Preliminary Report on the Effect of a Lower Dose of Gonadotropin-Releasing Hormone Antagonist (Cetrorelix) on Ovarian Hyperstimulation in Lower-Weight Asian Women," Taiwanese J Obstet Gynecol, vol. 45, No. 4, pp. 317-320 (Dec. 2006).
Cordts et al., "P-455 Low dose of FSHr in controlled ovarian hyper stimulation response—experience of an assisted human reproduction center of low cost using 100 IU of FSHr", Fertility and Sterility, vol. 100, No. 3, Supplement (2013), p. S279-S280 doi:10.1016/j.fertnstert.2013.07.1158.
Dzik et al., "P-270 Comparison between two protocols of ovarian stimulation using a depot formulation of GnRH-agonist and a fixed-dose regimen of recombinant FSH: A prospective randomized study", Fertility and Sterility, vol. 82, Supplement 2 (2004), p. S231, doi:10.1016/j.fertnstert.2004.07.612.
Ferring Inc., "Product Monograph Including Patient Medication Information," Rekovelle, pp. 1-24, (Mar. 2018) XP05551627, Retrieved from the Internet, URL: https://pdf.hres.ca/dpd_pm/00044406.pdf [retrieved on Oct. 17, 2018].

(Continued)

*Primary Examiner* — Christina M Borgeest
(74) *Attorney, Agent, or Firm* — Foley & Lardner LLP

(57) ABSTRACT

Methods using and compositions including FSH for use in the treatment of infertility are described, wherein the dose is selected based on the patient's age to optimise cumulative efficiency and/or reduce OHSS risk.

6 Claims, No Drawings

(56) References Cited

OTHER PUBLICATIONS

Gomaa et al., "Addition of low dose hCG to rFSh benefits older women during ovarian stimulation for IVF," Reproductive Biology and Endocrinology, Biomed Central Ltd, GB, vol. 10, No. 1, p. 55, XP021116085 (Aug. 2012).
Joan-Carles Arce et al., "Ovarian response to recombinant human follicle-stimulating hormone: a randomized, antimuellerian hormone-stratified, dose-response trial in women undergoing in vitro fertilization/intracytoplasmic sperm injection," Fertility and Sterility, vol. 102, No. 6, pp. 1633-1640, Supplemental pp. 1640.e1-1640.e5, XP009512600 (Dec. 2014).
Karlsson et al., "A population model for the follicular growth in women treated with follicle stimulating hormone," Clinical Pharmacology and Therapeutics, vol. 62, No. 6, pp. 665-674, XP055658125 (Dec. 1997).
Olivennes, F. et al.: "Individualizing FSH dose for assisted reproduction using a novel algorithm: the CONSORT study", Reproductive Biomedicine Online, vol. 18, No. 2 (2009), pp. 195-204 https://www.rbmojournal.com/article/S1472-6483(10)60256-8/pdf.
Sterrenburg et al., "Clinical outcomes in relation to the daily dose of recombinant follicle-stimulating hormone for ovarian stimulation in in vitro fertilization in presumed normal responders younger than 39 years: a meta-analysis," Human Reproduction Update, vol. 17, No. 2, pp. 184-196, XP055658116 (Mar. 2011).
The Practice Committee of the American Society for Reproductive Medicine, et al., "Gonadotripin preparations: past, present, and future perspectives," Fertility and Sterility, Elsevier Science Inc., New York, NY, vol. 90, Suppl 3, pp. S13-S20, XP025655883 (Nov. 2008).
The Latin-American Puregon IVF Study Group, "A double-blind clinical trial comparing a fixed daily dose of 150 and 250 IU of recombinant follicle-stimulating hormone in women undergoing in vitro fertilization," Fertility and Sterility, vol. 76, No. 5, pp. 950-956, Nov. 2001.
Communication pursuant to Article 94(3) EPC received in European Patent Application No. 19794444.0 dated Sep. 29, 2023.
N.V. Organon; "Puregon—Summary of product characteristics" European Medicines Agency, Jul. 31, 2009; XP093086084.
Benjamin Leader et al. "High frequency of discordance between anti-mullerian hormone and follicle-stimulating hormone levels in serum from estradiol-confirmed days 2 to 4 of the menstrual cycle from 5,354 women in U.S. fertility centers" Reproductive Endocrinology; vol. 98 No. 4. 1040-1042; Oct. 2012.
Dias and Ulloa-Aguirre, "New Human Follitropin Preparations: How Glycan Structural Differences May Affect Biochemical and Biological Function and Clinical Effect" Frontiers in Endocrinology (Mar. 19, 2021) 12:636038, doi: 10.3389/fendo.2021.636038.
Doody et al., "Ovarian Stimulation With FE 999049 is Efficacious and Safe in Women 35-42 Years of Age: Primary Findings of the RITA-2 Registration Trial" Fertility and Sterility, vol. 120, Issue 4, e101 (Oct. 18, 2023).
Loutradis et al., "FSH receptor gene polymorphisms have a role for different ovarian response to stimulation in patients entering IVF/ICSI-ET programs" Journal of Assisted Reproduction and Genetics, vol. 23, No. 4, Apr. 2006.
Office Action dated Aug. 26, 2024, received in Korean Patent Application No. 10-2021-7008853.
Olsson et al., Different Pharmacokinetic and Pharmacodynamic Properties of Recombinant Follicle-Stimulating Hormone (rFSH) Derived From a Human Cell Line Compared With rFSH From a Non-Human Cell Line J. Clin. Pharmacol. Apr. 30, 2024, 54(11): 1299-1307.
Seifer et al., "Age-specific serum anti-Meullerian hormone values for 17,120 women presenting to fertility centers within the United States" Fertil. Steril. (Feb. 2011) 95(2): 747-750.
Sudo et at., "Genetic and functional analyses of polymorphisms in the human FSH receptor gene" Molecular Human Reproduction vol. 8, No. 10 pp. 893-899, (Jul. 31, 2002).

\* cited by examiner

COMPOSITIONS AND METHODS FOR CONTROLLED OVARIAN STIMULATION

CROSS-REFERENCE TO RELATED APPLICATIONS

The present application is the U.S. National Stage of International Application No. PCT/EP2019/078170, filed Oct. 17, 2019, and claims priority to U.S. Provisional Patent Application No. 62/746,812, filed Oct. 17, 2018, and European Patent Application No. 18203167.4, filed Oct. 29, 2018.

The present invention relates to methods, compositions and pharmaceutical products for the treatment of infertility.

BACKGROUND

Assisted reproductive technologies (ART) such as in vitro fertilisation (IVF) and microinsemination are well known. ART generally requires a step of controlled ovarian stimulation (COS), in which a cohort of follicles is stimulated to full maturity. Standard COS regimens include administration of gonadotrophins, such as follicle stimulating hormone (FSH), alone or in combination with luteinising hormone (LH) activity to stimulate multiple follicular development. Usually COS requires administration of a GnRH analogue, or GnRH agonist, prior to and/or during stimulation to prevent a premature LH surge which may induce ovulation before planned oocyte retrieval. The pharmaceutical compositions generally used for COS include recombinant follicle stimulating hormone (rFSH) including REKOVELLE® and GONAL-F®, urinary derived FSH, recombinant FSH+LH preparations, urinary derived menotrophin [human menopausal gonadotrophin (hMG)] and highly purified human menopausal gonadotrophin (HP-hMG).

In case of a too high ovarian response, COS can be associated with a risk of ovarian hyperstimulation syndrome (OHSS), which can become life threatening in severe cases. The ability to predict the ovarian response potential of women to COS may allow the development of personalised or individualised COS protocols. Such individualised protocols could, for example, reduce the risk of OHSS in women predicted to have an excessive ovarian response to COS, and/or improve the chance of pregnancy in women classed as poor responders. Levels of AMH are directly correlated with the ovarian response to gonadotrophins during COS. Thus, high levels of AMH are a good predictor of excessive ovarian response, and an indicator of risk of OHSS, whereas low levels of AMH predict a poor ovarian response to COS.

Clinical research has focused the last years on the development of individualised dosing regimens for COS, initially without using AMH but based on other predictors of ovarian response. These predictors include age, body mass index (BMI), FSH, and antral follicle count (AFC).

As indicated above, standard COS protocols require daily FSH administration to induce multiple follicular growth to obtain sufficient oocytes for IVF. FSH is a natural hormone that is secreted by the anterior pituitary gland. In healthy women FSH induces monthly the growth of a single dominant follicle that ovulates during each natural cycle. FSH purified from the urine of post-menopausal women has been used for many years in infertility treatment, both to promote ovulation in natural reproduction and to induce multiple follicular growth to obtain sufficient oocytes for ART.

Until recently, the only approved rFSH products for ovarian stimulation, such as follitropin alfa (GONAL-F®, Merck Serono/EMD Serono) and follitropin beta (PUREGON®/FOLLISTIM®, MSD/Schering-Plough), were derived from a Chinese Hamster Ovary (CHO) cell line. The present applicants have developed a human cell line-derived rFSH which is the subject of International Patent Application No. PCT/GB2009/000978, published as WO2009/127826A. On 13 Dec. 2016, the European Commission (EC) granted marketing authorisation for REKOVELLE® (follitropin delta, also known as FE 999049), a human cell line-derived recombinant follicle stimulating hormone (human rFSH), for use in controlled ovarian stimulation for the development of multiple follicles in women undergoing assisted reproductive technologies (ART), such as an in vitro fertilisation (IVF) cycle. REKOVELLE® is the first rFSH to be derived from a human cell line. The REKOVELLE® (follitropin delta) product is produced by the methods disclosed in International Patent Application No. PCT/GB2009/000978.

The posology of REKOVELLE® is individualised for each patient and aims to obtain an ovarian response which is associated with a favourable safety/efficacy profile, i.e. aims to achieve an adequate number of oocytes retrieved and reduce the interventions to prevent OHSS. REKOVELLE® is dosed in micrograms (μg). For the first treatment cycle, the individual daily dose is determined on the basis of the woman's serum AMH concentration and, depending on serum AMH concentration, her body weight. The dose is based on a recent determination of AMH (i.e. within the last 12 months) measured by the ELECSYS® AMH Plus immunoassay (Roche). The individual daily dose is maintained throughout the stimulation period. For women with AMH<15 pmol/L the daily dose of REKOVELLE® is 12 μg, irrespective of body weight. For women with AMH≥15 pmol/L the daily dose of REKOVELLE® is lower, and ranges from 0.19 μg/kg to 0.10 μg/kg over AMH concentrations of 15 to ≥40 pmol/L. For subsequent treatment cycles, the daily dose of REKOVELLE® is maintained or modified according to the patient's ovarian response in the previous cycle. If the patient had adequate ovarian response in the previous cycle without developing OHSS, the same daily dose is used. In case of ovarian hypo-response in the previous cycle, the daily dose in the subsequent cycle is increased by 25% or 50%, according to the extent of response observed. In case of ovarian hyper-response in the previous cycle, the daily dose in the subsequent cycle is decreased by 20% or 33%, according to the extent of response observed. In patients who developed OHSS or were at risk of OHSS in a previous cycle, the daily dose for the subsequent cycle is 33% lower than the dose the cycle where OHSS or risk of OHSS occurred. The maximum daily dose of REKOVELLE® is 24 μg.

Still, there is a need for COS protocols which provide adequate response to stimulation and/or decreased risk of OHSS.

SUMMARY

In accordance with some aspects, there are provided compositions comprising recombinant follicle stimulating hormone (rFSH) for use in the treatment of infertility in a patient of age 35 years, wherein the composition is for administration at a (e.g., starting) dose of, or a (e.g., starting) dose equivalent to, 15 μg rFSH per day. Also provided are compositions for use in the treatment of infertility in a patient of age≥35 years, wherein the composition comprises a (e.g., starting) dose of, or a (e.g., starting) dose equivalent to, 15 µg rFSH per day. The composition may be for administration at a (e.g., starting) dose of 15 µg rFSH per day.

In accordance with some aspects, there are provided compositions comprising rFSH for use in the treatment of infertility in a patient of age≥35 years, wherein the composition is for administration at a starting dose of 15 µg rFSH per day, wherein the starting dose is administered on at least day 1 of treatment (preferably on at least day 1 and day 2 of treatment, more preferably on each of days 1 to 4 of treatment), optionally wherein the dose is (i) increased by a first incremental dose increase of 3 µg recombinant FSH on any subsequent day of treatment; and/or (ii) decreased by a first incremental dose decrease of 3 µg recombinant FSH on any subsequent day of treatment. The dose may be maintained at the starting dose for the duration of the treatment. Alternatively, a first incremental dose increase of 3 µg rFSH may be (a) followed by at least one further incremental dose increase of 3 µg rFSH at least two days after the previous incremental change in dose; and/or (b) followed by at least one incremental dose decrease of 3 µg rFSH at least one day after the previous incremental change in dose. Additionally or alternatively, a first incremental dose decrease of 3 µg rFSH may be (a) followed by at least one incremental dose increase of 3 µg rFSH at least two days after the previous incremental dose change in dose; and/or (b) followed by at least one further incremental dose decrease of 3 µg rFSH at least one day after the previous change in dose. The dose may be increased to a maximum daily dose of 24 µg or decreased to a minimum daily dose of 6 µg.

In accordance with some aspects, there are provided compositions comprising rFSH for use in the treatment of infertility in a patient identified as being of ages≤34 years, wherein the composition is for administration at a (e.g., starting) dose of, or a (e.g., starting) dose equivalent to, 12 µg rFSH per day. Also provided are compositions for use in the treatment of infertility in a patient identified as being of ages≤34 years, wherein the composition comprises a (e.g., starting) dose of, or a (e.g., starting) dose equivalent to, 12 µg rFSH per day. The composition may be for administration at a (e.g., starting) dose of 12 µg rFSH per day.

In accordance with some aspects, there are provided compositions comprising rFSH for use in the treatment of infertility in a patient of ages≤34 years, wherein the composition is for administration at a starting dose of 12 µg rFSH per day, wherein the starting dose is administered on at least day 1 of treatment (preferably on at least day 1 and day 2 of treatment, more preferably on each of days 1 to 4 of treatment), optionally wherein the dose is (i) increased by a first incremental dose increase of 3 µg rFSH on any subsequent day of treatment; and/or (ii) decreased by a first incremental dose decrease of 3 µg rFSH on any subsequent day of treatment.

The dose may be maintained at the starting dose for the duration of the treatment. Additionally or alternatively, a first incremental dose increase of 3 µg rFSH may be (a) followed by at least one further incremental dose increase of 3 µg rFSH at least two days after the previous incremental change in dose; and/or (b) followed by at least one incremental dose decrease of 3 µg rFSH at least one day after the previous incremental change in dose. Additionally or alternatively, a first incremental dose decrease of 3 µg rFSH may be (a) followed by at least one incremental dose increase of 3 µg rFSH at least two days after the previous incremental dose change in dose; and/or (b) followed by at least one further incremental dose decrease of 3 µg rFSH at least one day after the previous change in dose. The dose may be increased to a maximum daily dose of 24 µg or decreased to a minimum daily dose of 6 µg.

In accordance with some aspects, there are provided methods of treating infertility in a female patient age≥35 years, comprising administering recombinant follicle stimulating hormone (rFSH) at a dose of, or a dose equivalent to, 15 µg rFSH per day starting on day 1 of treatment. The rFSH may be administered at a dose of 15 µg rFSH per day starting on day 1 of treatment.

In accordance with some aspects, the method comprises administering rFSH at a starting dose of 15 µg per day for at least 1-4 days; and, optionally, on any subsequent day, (i) increasing the dose of rFSH by an incremental dose increase of 3 µg rFSH or (ii) decreasing the dose of rFSH by an incremental dose decrease of 3 µg rFSH. The rFSH dose may be maintained at the starting dose of 15 µg per day throughout the treatment. Additionally or alternatively, an incremental dose increase of 3 µg rFSH may be followed by (a) a further incremental dose increase of 3 µg rFSH at least two days after the previous incremental dose increase or (b) an incremental dose decrease of 3 µg rFSH at least one day after the previous incremental dose increase. Additionally or alternatively, an incremental dose decrease of 3 µg rFSH may be followed by (a) an incremental dose increase of 3 µg rFSH at least one day, or at least two days, after the previous incremental dose decrease or (b) a further incremental dose decrease of 3 µg rFSH at least one day after the previous incremental dose decrease. In accordance with some aspects, throughout the treatment the maximum daily dose of rFSH is 24 µg and the minimum daily dose is 6 µg.

In accordance with some aspects, there are provided methods of treating infertility in a female patient identified as being of ages≤34 years, comprising administering rFSH at a dose of, or a dose equivalent to, 12 µg rFSH per day starting on day 1 of treatment. The rFSH may be administered at a dose of 12 µg rFSH per day starting on day 1 of treatment.

In accordance with some aspects, the method comprises administering rFSH at a starting dose of 12 µg per day for at least 1-4 days; and, optionally, on any subsequent day, (i) increasing the dose of rFSH by an incremental dose increase of 3 µg rFSH or (ii) decreasing the dose of rFSH by an incremental dose decrease of 3 µg rFSH. The rFSH dose may be maintained at the starting dose of 12 µg per day throughout the treatment. Additionally or alternatively, an incremental dose increase of 3 µg rFSH is followed by (a) a further incremental dose increase of 3 µg rFSH at least two days after the previous incremental dose increase or (b) an incremental dose decrease of 3 µg rFSH at least one day after the previous incremental dose increase. Additionally or alternatively, an incremental dose decrease of 3 µg rFSH is followed by (a) an incremental dose increase of 3 µg rFSH at least one day, or at least two days, after the previous incremental dose decrease or (b) a further incremental dose decrease of 3 µg rFSH at least one day after the previous incremental dose decrease. In accordance with some aspects, throughout the treatment the maximum daily dose of rFSH is 24 µg and the minimum daily dose is 6 µg.

In accordance with some aspects, there are provided methods of treating infertility in a female patient, comprising determining the age of the patient; if the patient is age≥35 years, administering recombinant follicle stimulating hormone (rFSH) at a starting dose of 15 µg rFSH per day for at least 1-4 days; if the patient is ages≤34 years, administering rFSH at a starting dose of 12 µg rFSH per day for at least 1-4 days; optionally, on any subsequent day, (i)

increasing the dose of rFSH by an incremental dose increase of 3 µg rFSH or (ii) decreasing the dose of rFSH by an incremental dose decrease of 3 µg rFSH, wherein, throughout the treatment, the maximum daily dose of rFSH is 24 µg and the minimum daily dose is 6 µg.

In accordance with any embodiments, the treatment of infertility may comprise a step of determining the age of the patient, and a step of administering the defined dose of rFSH to a patient having the defined age. In accordance with any embodiments, the treatment of infertility may comprise determining the age of the patient, and then administering the starting dose of rFSH described herein for the patient's age.

In accordance with any embodiments, the treatment of infertility further comprises retrieving (e.g. harvesting) oocyte(s); fertilizing (e.g. inseminating) the oocytes (s); and allowing the fertilized oocytes to develop to the blastocyst stage. In accordance with any embodiments, the treatment of infertility further comprises assessing the quality of blastocysts obtained after fertilization of the harvested oocytes.

In accordance with any embodiments, the treatment of infertility step of monitoring the patient for over-response to treatment by identifying, during treatment, a patient with ≥20 follicles with a diameter of ≥12 mm and/or a serum estradiol concentration ≥3,000 pg/mL; and optionally administering a dose of GnRH agonist (e.g. 4.0 mg) to the patient identified during treatment as having ≥20 follicles with a diameter of ≥12 mm and/or a serum estradiol concentration ≥3,000 pg/mL.

In accordance with any embodiments, patient may be over 30 years of age and/or previously failed at least one cycle of infertility treatment.

In accordance with any embodiments, the rFSH may include α2,6-sialylation and α2,3-sialylation, optionally wherein 1% to 50% of the total sialylation is α2, 6-sialylation, and 50% to 99% of the total sialylation is a 2,3-sialyation, optionally wherein 5% to 20% of the total sialylation is α2, 6-sialyation, and 80% to 95% of the total sialylation is 2,3-sialyation, optionally wherein 50% to 80% of the total sialylation is α2, 6-sialyation, and 20% to 50% of the total sialylation is 2,3-sialyation.

In accordance with any embodiments, the treatment of infertility is for development of multiple follicles and pregnancy after fresh and/or cryopreserved embryo transfer in ovulatory women undergoing assisted reproductive technology (ART). In accordance with any embodiments, the treatment of infertility is for optimising cumulative efficiency and/or reducing ovarian hyperstimulation syndrome (OHSS) risk.

DETAILED DESCRIPTION

The present applicants have now developed a dosing protocol with the aim of maximizing both oocyte yield and resultant cumulative pregnancy rates while maintaining safety. The applicants have devised COS protocols wherein specific doses of recombinant FSH are used to treat patients based on their age, thereby increasing the likelihood of adequate response to stimulation (e.g., in patients having a low response potential), and/or decreased risk of OHSS (e.g., in patients classed as high or excessive responders). Also provided are protocols and compositions for treatment of patients with high ovarian response through use of a GnRH agonist trigger and cryopreserved embryo transfer-only cycles for those patients.

With regard to efficacy, the outcome variable defining ART success now goes beyond the initial fresh transfer of the embryos/blastocyst. Cryopreservation of surplus embryos for potential use after the fresh cycle now is standard practice in ART treatment, and serves to improve chances of pregnancy from a single stimulation cycle. The percentage of transfer cycles involving cryopreserved embryos has steadily increased over recent years. Thus, the cumulative outcomes from both the fresh and subsequent cryopreserved cycles provide an overall measure of a clinical efficacy of a single controlled ovarian stimulation cycle in a more complete manner and reflects the evolution in clinical management of infertility.

With regard to safety, implementation of a gonadotropin-releasing hormone (GnRH) agonist trigger improves patient safety by reducing the risk of early severe ovarian hyperstimulation syndrome (OHSS), which impairs the efficacy in a fresh transfer perspective but does not compromise the overall efficacy based on a cumulative pregnancy rate perspective. Implementation of GnRH agonist triggering in patients with excessive response to reduce the risk of OHSS, as well as implementation of mandatory single blastocyst transfer to maximize the incidence of singletons and reduce the risk of multiple gestation, address the most common safety concerns.

Therefore, provided herein are dosing regimens constructed to establish a high cumulative ongoing pregnancy rate by a safe high dose while minimizing the risk for OHSS, especially moderate and severe OHSS, such as by using GnRH agonist triggering in case of excessive response.

Definitions

Technical and scientific terms used herein have the meanings commonly understood by one of ordinary skill in the art of assisted reproductive technology to which the present invention pertains, unless otherwise defined. Reference is made herein to various methodologies known to those of ordinary skill in the art. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

It is to be understood, that any definitions and terms herein defined is meant to have the same meaning and purpose in any of the aspects and embodiments of the invention unless explicitly otherwise stated not to.

As used herein, the singular forms "a," "an," and "the" designate both the singular and the plural, unless expressly stated to designate the singular only.

As used herein, the term "about" means that the number or range is not limited to the exact number or range set forth, but encompass ranges around the recited number or range as will be understood by persons of ordinary skill in the art depending on the context in which the number or range is used. Unless otherwise apparent from the context or convention in the art, "about" mean up to plus or minus 10% of the particular term.

Herein the terms "patient" and "subject" are used interchangeably.

A subject may have normal serum FSH level of 1 to 16 IU/L, for example 1 to 15 IU/L, for example 1 to 12 IU/L in the early follicular phase. Thus a composition or medicament as described herein may be for (use in) the treatment of infertility (and/or for controlled ovarian stimulation) in a subject having normal serum FSH level of 1 to 16 IU/L, for example 1 to 15 IU/L, for example 1 to 12 IU/L in the early follicular phase.

A subject may have a BMI>1 and BMI<40 kg/m², for example a BMI>17.5 and BMI<38 kg/m², for example a BMI>18 and BMI<25 kg/m², for example a BMI>20 and BMI<25 kg/m². Thus a product as described herein may be for (use in) the treatment of infertility (and/or for controlled ovarian stimulation) in a subject having BMI>1 and BMI<40 kg/m², for example a subject having BMI>17.5 and BMI<38 kg/m², for example a subject having BMI>18 and BMI<25 kg/m², for example a subject having BMI>20 and BMI<25 kg/m².

Herein the term "treatment of infertility" includes treatment of infertility by controlled ovarian stimulation (COS) or methods which include a step or stage of controlled ovarian stimulation (COS), for example in vitro fertilisation (IVF), or intracytoplasmic sperm injection (ICSI). The term "treatment of infertility" includes treatment of infertility in a subject having tubal or unexplained infertility, including treatment of infertility in a subject having endometriosis, for example stage I or stage II endometriosis, and/or in a subject with a partner with male factor infertility. The composition may be for (use in) the treatment of infertility (and/or for controlled ovarian stimulation) in a subject having endometriosis, for example in a subject having stage I or stage II endometriosis, as defined by The American Society for Reproductive Medicine (ASRM) classification system for the various stages of endometriosis, (stage IV most severe; stage I least severe) [American Society for Reproductive Medicine. Revised American Society for Reproductive Medicine classification of endometriosis: 1996. Fertil Steril 1997; 67,817 821.].

Herein the term "GnRH agonist" means gonadotropin-releasing hormone agonist. GnRH agonists are a class of medications that act as agonists of the gonadotropin-releasing hormone receptor (GnRH receptor), the biological target of gonadotropin-releasing hormone.

Herein the term "GnRH antagonist" means gonadotropin-releasing hormone antagonist. GnRH antagonists are a class of medications that antagonize the gonadotropin-releasing hormone receptor (GnRH receptor) and thus the action of gonadotropin-releasing hormone (GnRH).

The term "follicle" herein means an ovarian follicle which is a fluid-filled sac that contains an immature egg, or oocyte.

A blastocyst forms in the early development of a human (or other mammal). In humans, blastocyst formation begins about 5 days after fertilization. The use of blastocysts in (IVF) generally involves retrieval (harvesting) from the woman a number of oocytes resulting from a controlled ovarian stimulation cycle; fertilization (insemination of) one or more oocytes and culturing the fertilized egg (oocyte) for five days to form a blastocyst (i.e. allowing the fertilized oocyte to develop to the blastocyst stage); and implanting the blastocyst into the uterus.

In accordance with all aspects described herein, it is preferred that the treatment of infertility described herein, is or includes, a step of COS. The cause of infertility could be the woman's partner suffering from male infertility, although it will be appreciated that according to the present invention it is the woman (female) who is treated by COS.

A treatment of infertility as described herein may be for, and may be effective for, development of multiple follicles and pregnancy after fresh and/or cryopreserved embryo transfer in ovulatory women undergoing assisted reproductive technology (ART).

A treatment of infertility as described herein may be for, and may be effective for, promoting good quality blastocysts (e.g., category 3BB or higher blastocysts, e.g., treatment of infertility to increase the number of category 3BB or higher blastocysts on day 5 after oocyte retrieval) and/or to improve embryo implantation. The treatment of infertility may be treatment of infertility to increase the number of category 3BB or higher blastocysts on day 5 after oocyte retrieval (e.g., as compared to treatment with GONAL-F®). The treatment of infertility may be treatment of infertility to increase the number of fertilised (2PN) oocytes (e.g., as compared to treatment with GONAL-F®).

As used herein, "day one of treatment", also referred to as "day one of stimulation", refers to the first day that the dose of (e.g., recombinant) FSH is administered to the patient. Day one of treatment (stimulation) may take place on day 1, 2 or 3, for example on day 2 or day 3, of the patient's menstrual cycle. In other words, day one of treatment (stimulation) may be one, two or three days, for example two or three days, after the patient commences menstrual bleeding, consistent with usage of this term in clinical practice with GnRH antagonist or GnRH agonist protocols. The term "during treatment" means on a day or on days that FSH is being administered to the patient.

In the treatments described herein, the administration of recombinant FSH starts on day one of treatment and may continue for two to twenty days, for example continue for 2, 3, 4, 5, 6, 7, 8, 9, 10, 11, 12, 13, 14, 15, 16, 17, 18, 19, or 20 days. The dose administered on day 1 is referred to herein as the "starting dose". The administration of recombinant FSH starts on day one of treatment and may continue for four to twenty days, for example seven to thirteen days, for example nine to thirteen days, for example 10 to 13 days, for example 10 to 11 days. The dose may be the same every day. However, variation of the dose depending on the patient's ovarian response (e.g., as measured by ultrasonography) is more likely.

In accordance with all aspects described herein, the recombinant FSH may be human cell line-derived recombinant FSH as described in more detail below. In all aspects, the recombinant FSH may be that sold under the trademark REKOVELLE® (follitropin delta) (Ferring B.V.). In all aspects, the recombinant FSH may be administered by injection, e.g., subcutaneous injection.

In accordance with all aspects described herein, the recombinant FSH composition (e.g., pharmaceutical composition) or medicament may be administered after pre-treatment of the patient with a (different) pharmaceutical composition, herein termed "composition A", which suppresses endogenous gonadotropin production prior to day one of the treatment with rFSH. In other words, the composition (e.g., pharmaceutical composition) or medicament may be administered after the subject has been (pre-) treated with composition A, wherein composition A is a steroid, a GnRH agonist, a GnRH antagonist, etc. Herein, the term "pre-treated" or "pre-treatment" refers to administration of the pharmaceutical composition which suppresses endogenous gonadotropin production prior to day one of the treatment with rFSH (i.e., prior to day 1 of treatment), consistent with usage of this term in clinical practice with long GnRH agonist protocols.

Thus, the composition (e.g., pharmaceutical composition) or medicament for use described herein may be for administration 12 to 16, e.g., 13 to 15, e.g., 14 days, after administration of (e.g., after initiation of administration of, e.g., after initiation of daily administration of) a GnRH agonist (e.g., SYNAREL®, LUPRON®, DECAPEP-TYL®). Additionally or alternatively, the recombinant FSH composition for use described herein may be for administration with a GnRH agonist.

Alternatively, the recombinant FSH composition (e.g., pharmaceutical composition) or medicament may be administered, or may be for administration, prior to administration of a GnRH antagonist (e.g., GANIRELIX®, CETRORELIX®), for example for administration five or six days prior to administration of a GnRH antagonist (i.e., for administration such that day 1 of stimulation is 5 or 6 days prior to administration of a GnRH antagonist). Additionally or alternatively, the recombinant FSH composition (e.g., pharmaceutical composition) for use described herein may be for administration with a GnRH antagonist.

Typically, in accordance with all aspects described herein, the recombinant FSH composition (e.g., pharmaceutical composition) or medicament is administered, or is for administration, prior to administration of a high (ovulatory) dose of human chorionic gonadotropin (hCG) (for example 4,000 to 11,000 IU hCG, e.g., 5,000 IU hCG, 10,000 IU hCG, etc.; or 150 to 500 µg recombinant hCG, for example 250 µg recombinant hCG); to induce final follicular maturation. Thus, in some embodiments, the methods described herein further comprise administration of a high (ovulatory) dose of human chorionic gonadotropin (hCG).

In accordance with all aspects described herein, the treatment of infertility described herein may further comprise: retrieving (e.g., harvesting) oocyte(s); fertilizing (e.g., inseminating) the oocytes (s); and allowing the fertilized oocytes to develop to the blastocyst stage. The fertilization (e.g., insemination) may be in vitro fertilization, optionally intra-cytoplasmic sperm injection (ICSI).

In accordance with all aspects described herein, the treatment of infertility described herein may further comprise assessing the quality of blastocysts obtained after fertilization of the harvested oocytes [e.g., to identify one or more good quality (i.e. grade 3BB or above) blastocysts]. Assessment of blastocyst quality may take place on day 5 after oocyte retrieval and may study three parameters: blastocyst expansion and hatching status (grade 1-6), blastocyst inner cell mass grading (grade A-D) and trophectoderm grading (grade A-D), as is well known in the art. Blastocysts can be given a numerical score by using the system of Gardner & Schoolcraft, as is well known in the art, with the addition of D-categories for inner cell mass and trophectoderm.

In accordance with all aspects described herein, the treatment of infertility described herein may further comprise transfer of one or more blastocyst(s) identified by assessment of quality of the blastocysts (e.g., fresh blastocyst transfer). In specific embodiments, a single blastocyst is transferred.

In accordance with all aspects described herein, the treatment of infertility described herein may further comprise freezing one or more blastocysts identified by assessment of quality of the blastocysts (for later transfer).

Thus, In accordance with all aspects described herein, the treatment of infertility described herein may further comprise—in addition to optional administration of a GnRH agonist or antagonist, administration of recombinant FSH, and administration of an ovulatory dose of hCG, retrieving (e.g., harvesting) oocyte(s); fertilizing (e.g., inseminating) the oocyte(s)—allowing the fertilized oocytes to develop to the blastocyst stage and cryopreserving one or more blastocysts (e.g., blastocysts identified by assessment of quality of the blastocysts, e.g., for later transfer).

The treatment of infertility described herein may be for, and may be effective for, optimising cumulative efficiency (i.e., maximising the patient's chance of successful pregnancy following fresh or subsequent cryopreserved cycle) and/or reducing OHSS risk (i.e. reducing the risk of OHSS by e.g., monitoring and/or control of over-response to treatment).

Treatments Reducing OHSS Risk

In accordance with all aspects described herein, a treatment of infertility described herein may include a step of monitoring the patient for over-response to treatment. Herein "over-response to treatment" is defined as a patient reaction to treatment which results in ≥20 follicles with a diameter of ≥12 mm and/or a serum estradiol concentration ≥3,000 pg/mL at any point in treatment. This step of monitoring the patient for over-response to treatment may comprise identifying, during treatment, a patient with ≥20 follicles with a diameter of 12 mm and/or a serum estradiol concentration ≥3,000 pg/mL.

In accordance with all aspects described herein, a treatment of infertility described herein may further comprise administering a dose of GnRH agonist (e.g., 4.0 mg) to a patient identified during treatment as having ≥20 follicles with a diameter of ≥12 mm and/or a serum estradiol concentration ≥3,000 pg/mL.

In accordance with all aspects described herein, a treatment of infertility described herein wherein the patient is identified during treatment as having ≥20 follicles with a diameter of ≥12 mm and/or a serum estradiol concentration ≥3,000 pg/mL, may further comprise retrieving (e.g., harvesting) oocyte(s); fertilizing (e.g., inseminating) the oocyte(s); allowing the fertilized oocytes to develop to the blastocyst stage; and cryopreserving one or more blastocysts (e.g., blastocysts identified by assessment of quality of the blastocysts, e.g., for later transfer). In this way, patients identified as over-responders (by their excessive number of large follicles and/or excessive serum estradiol level) may have a cryopreserved blastocyst thawed and transferred (frozen cycle, cryopreserved embryo transfer-only cycle) after their recovery from over-response.

The recombinant FSH doses listed herein may be for treatment of infertility in the patient's (subject's) first stimulation protocol (first stimulation "cycle") by the methods and treatment protocols described herein. Thus, the composition(s) may be for use in the treatment of infertility in a patient (subject) who has not previously been treated for infertility by controlled ovarian stimulation; for use in the treatment of infertility in a patient (subject) who has not previously completed a treatment for infertility by controlled ovarian stimulation; or for use in the treatment of infertility in a patient (subject) who has not been treated for infertility by controlled ovarian stimulation in the previous six months, more preferably a patient (subject) who has not been treated for infertility by controlled ovarian stimulation in the previous twelve months. It will be appreciated that for further stimulation cycles (that is, treatments of infertility by controlled ovarian stimulation) by the methods and treatment protocols described herein, the doses may be adjusted according to actual ovarian response in the first cycle by the methods and treatment protocols described herein.

Treatments for Patients Age ≥35 Years

In some aspects, the patient is a female patient of age≥35 years, such as age 35-42 years. The patient may be 35 or over 35 years of age. The patient may be 36 or over 36 years of age, or 37 or over 37 years of age, or 38 or over 38 years of age, or 39 or over 39 years of age, or 40 or over 40 years of age, or 41 or over 41 years of age, or 42 years of age.

The patient may have previously failed at least one cycle of infertility treatment (i.e., the patient may have previously completed a treatment by controlled ovarian stimulation but not become pregnant), such as a previous infertility treatment by a different protocol and/or using different therapeutic agents, such as GONAL-F® instead of rFSH.

In specific embodiments, the composition is for treatment of a patient over 35 years of age, the patient having have previously failed at least one cycle of infertility treatment (such as a previous infertility treatment by a different protocol and/or using different therapeutic agents). The patient may have previously failed up to three cycles of infertility treatment (such as by a different protocol and/or using different therapeutic agents).

The treatment of infertility may comprise a step of determining the age of the patient, and a step of administering a dose of recombinant FSH as described herein to a patient having age≥35 years. The step of identifying the patient (prior to treatment) based on the age of the patient may take place just before (e.g., 0 to 2 days before) a dose of rFSH is first administered to the patient (e.g., before a starting dose of rFSH is administered).

In a first aspect, there is provided a composition (e.g., a pharmaceutical composition) comprising recombinant follicle stimulating hormone (rFSH) for use in the treatment of infertility in a patient of (e.g., identified as being of) age≥35 years, wherein the composition is for administration at a dose of, or a dose equivalent to, 15 µg recombinant FSH per day. For example, the composition can be for administration at a dose of 15 µg recombinant FSH per day. The dose of recombinant FSH may be administered at a dose equivalent to the daily doses mentioned above. For example, the composition may be for administration at a dose of 15 µg recombinant FSH every day, or less typically at an equivalent of 45 µg recombinant FSH every three days (e.g., for administration on days 1, 4, 7 and so on).

In a further aspect, there is provided a composition (e.g., a pharmaceutical composition) for use in the treatment of infertility in a patient of (e.g., identified as being of) age≥35 years, wherein the composition comprises a dose of, or a dose equivalent to, 15 µg recombinant follicle stimulating hormone (FSH) per day. For example, the composition can be for administration at a dose of 15 µg recombinant FSH per day.

Also provided are methods of treating infertility in a patient in need thereof being of (e.g., identified as being of) age≥35 years, comprising administering to the patient recombinant follicle stimulating hormone (rFSH) at a dose of, or a dose equivalent to, 15 µg recombinant FSH per day. As noted above, the administration of recombinant FSH starts on day one of treatment and may continue for two to twenty days. The dose may be the same every day. However, variation of the dose depending on the patient's ovarian response (e.g., as measured by ultrasonography) is more likely.

As noted above, the recombinant FSH composition (e.g., pharmaceutical composition) or medicament may be administered after pre-treatment of the patient with a (different) pharmaceutical composition, herein termed "composition A", which suppresses endogenous gonadotropin production prior to day one of the treatment with rFSH, such as a steroid, a GnRH agonist, a GnRH antagonist etc.

As noted above, typically, the recombinant FSH composition (e.g., pharmaceutical composition) or medicament is administered, or is for administration, prior to administration of a high (ovulatory) dose of human chorionic gonadotropin (hCG) (for example, 4,000 to 11,000 IU hCG, e.g., 5,000 IU hCG, 10,000 IU hCG, etc.; or 150 to 500 µg recombinant hCG, for example 250 µg recombinant hCG); to induce final follicular maturation. In some embodiments, therefore, the methods described herein further comprise administration of a high (ovulatory) dose of human chorionic gonadotropin (hCG).

As noted above, the treatment of infertility may further comprise: retrieving (e.g., harvesting) oocyte(s); fertilizing (e.g., inseminating) the oocytes (s); and allowing the fertilized oocytes to develop to the blastocyst stage. As noted above, the treatment of infertility may further comprise assessing the quality of blastocysts and fresh transfer of blastocyst(s) or freezing of blastocysts for later transfer.

As noted above, the treatment may further comprise monitoring and/or control of over-response to treatment (e.g., OHSS).

According to a further aspect, there are provided methods of treating infertility in a patient of age≥35 years, and a composition comprising recombinant follicle stimulating hormone (FSH) for use in the treatment of infertility in a patient of age≥35 years, wherein the methods comprise, or composition is for, administration at a starting dose of 15 µg recombinant FSH per day, wherein the starting dose is administered on at least day 1 of treatment (for example on at least day 1 and day 2 of treatment, for example on each of days 1 to 4 of treatment), optionally wherein the dose is (i) increased by a first incremental dose increase of 2 to 4 µg rFSH (including 3 µg rFSH) on any subsequent day of treatment; and/or (ii) decreased by a first incremental dose decrease of 2 to 4 µg rFSH (including 3 µg rFSH) on any subsequent day of treatment.

The dose may be maintained at the starting dose for the duration of the treatment. The dose may be the same every day. However, variation of the dose e.g., depending on the patient's ovarian response (e.g., depending on follicular growth, e.g., as measured by ultrasonography) is more likely.

The method of treating infertility may include monitoring the patient's ovarian response to administration of rFSH (e.g., monitoring follicular growth, e.g., as measured by ultrasonography). The method of treating infertility may include monitoring the patient's ovarian response to administration of rFSH (e.g., monitoring follicular growth, e.g., as measured by ultrasonography) and, depending on follicular growth, increasing or decreasing the dose by 2 to 4 µg rFSH (including 3 µg rFSH). The method of treating infertility may include monitoring the patient's ovarian response to administration of rFSH (e.g., monitoring follicular growth, e.g. as measured by ultrasonography) on one or more days throughout the course of treatment, such as on one or more of day 5, day 7, day 9, day 11, day 13, day 15, day 17 and day 19 of treatment. The method of treating infertility may include monitoring the patient's ovarian response to administration of rFSH (e.g., a step of monitoring follicular growth, e.g., as measured by ultrasonography) on one or more days throughout the course of treatment, such as on one or more of day 5, day 7, day 9, day 11, day 13, day 15, day 17 and day 19 of treatment, and, depending on follicular growth, increasing or decreasing the dose by 2 to 4 µg rFSH (including 3 µg rFSH). That is, the dose may be increased or decreased depending on follicular growth on one or more days throughout the course of treatment, such as on one or more of day 5, day 7, day 9, day 11, day 13, day 15, day 17 and day 19 of treatment.

The dose may be increased in increments during treatment, decreased in increments during treatment, or be varied during treatment by both incremental dose increases and incremental dose decreases. Typically, dose increases are not implemented more frequently than once every 2 days; that is, a second incremental dose increase is not implemented until at least two days after a first incremental dose increase. This gradual increase constitutes a safe approach, and permits the treating physician to assess ovarian response to a given dose level before possibly increasing the dose. For example, the treating physician may decrease the dose for subjects with follicular growth indicating that a dose reduction would be an appropriate course of action. Dose decreases may be implemented as frequently as every day. The dose may be increased to a maximum daily dose of 24 µg rFSH or decreased to a minimum daily dose of 6 µg rFSH.

Thus, a first incremental dose increase of 2 to 4 µg rFSH (including 3 µg rFSH) may be (a) followed by a further incremental dose increases of 2 to 4 µg rFSH (including 3 µg rFSH) at least two days after the previous incremental increase in dose; and/or (b) followed by an incremental dose decrease of 2 to 4 µg rFSH (including 3 µg rFSH) at least one day after the previous incremental increase in dose. A first incremental dose decrease of 2 to 4 µg rFSH (including 3 µg rFSH) may be (a) followed by an incremental dose increase of 2 to 4 µg rFSH (including 3 µg) rFSH at least one day, or at least two days, after the previous incremental decrease in dose; and/or (b) followed by at a further incremental dose decrease of 2 to 4 µg rFSH (including 3 µg rFSH) at least one day after the previous incremental decrease in dose.

It will be appreciated that this aspect contemplates, for example, a dose of 15 µg recombinant FSH per day from day 1 of treatment to day 4 of treatment, the dose being increased in subsequent days of treatment by at least one increment of, e.g., 3 µg rFSH to 18 µg rFSH (e.g., on day 5 or 6). The dose of 18 µg rFSH may be continued to the end of treatment, or there may be one or two further incremental dose increases of, e.g., 3 µg rFSH to 21 µg rFSH, or to 21 µg rFSH and then to the maximum dose of 24 µg rFSH, with each incremental dose increase being at least two days after the previous incremental dose increase, or the dose being varied by both incremental dose increases and incremental dose decreases, each at the appropriate interval after the previous incremental dose change, such as may be warranted in view of the patient's ovarian response, as discussed above. Similarly, an initial dose reduction of, e.g., 3 µg rFSH to 12 µg rFSH (e.g., on day 5 or 6) may be implemented and that dose continued to the end of treatment, or there may be one or two further incremental dose decreases of, e.g., 3 µg rFSH to 9 µg rFSH, or to 9 µg rFSH and then to the minimum dose of 6 µg rFSH, with each decrease being at least one day after the previous incremental dose decrease, or the dose being varied by both incremental dose increases and incremental dose decreases, each at the appropriate interval after the previous incremental dose change, such as may be warranted in view of the patient's ovarian response, as discussed above. This aspect provides a means of varying the FSH dose in a safe manner based on the patient's response.

As with the first aspect discussed above, treatment in accordance with this aspect may further comprise administration of a high (ovulatory) dose of human chorionic gonadotropin (hCG), and, optionally, retrieving (e.g., harvesting) oocyte(s); fertilizing (e.g., inseminating) the oocytes (s); allowing the fertilized oocytes to develop to the blastocyst stage, further optionally assessing the quality of blastocysts and fresh transfer of blastocyst(s) or freezing of blastocysts for later transfer. Additionally or alternatively, the treatment may further comprise monitoring and/or control of over-response to treatment (e.g., OHSS).

Treatments for Patients Ages ≤34 Years

In some aspects, the patient is a female patient of ages≤34 years, such as from 18-34 years of age. The patient may be 34 or under 34 years of age, for example 33 or under 33 years of age, for example 30 or under 30 years of age, for example 28 or under 28 years of age.

The patient may have previously failed at least one cycle of infertility treatment, such as a previous infertility treatment by a different protocol and/or using different therapeutic agents, as discussed above. In a specific example, the composition is for treatment of a patients 34 years of age, the patient having have previously failed at least one cycle of infertility treatment (such as a previous infertility treatment by a different protocol and/or using different therapeutic agents). In a specific example, the composition is for treatment of a patient 30 to 34 years of age, the patient having have previously failed at least one cycle of infertility treatment (such as a previous infertility treatment by a different protocol and/or using different therapeutic agents). The patient may have previously failed up to three cycles of infertility treatment (such as by a different protocol and/or using different therapeutic agents).

The treatment of infertility may comprise a step of determining the age of the patient, and a step of administering the dose of recombinant FSH to a patient having ages≤34 years of age. The step of identifying the patient (prior to treatment) based on the age of the patient may take place just before (e.g., 0 to 2 days before) the first dose of rFSH is administered to the patient, for example, to determine or confirm the appropriate starting dose of rFSH.

In a further aspect there is provided a composition (e.g., pharmaceutical composition) comprising recombinant follicle stimulating hormone (FSH) for use in the treatment of infertility in a patient identified as being of ages≤34 years, wherein the composition is for administration at a dose of, or a dose equivalent to, 12 µg recombinant FSH per day. For example, the composition is for administration at a dose of 12 µg recombinant FSH per day.

In a further aspect there is provided a composition (e.g., pharmaceutical composition) for use in the treatment of infertility in a patient identified as being of ages≤34 years, wherein the composition comprises a dose of, or a dose equivalent to, 12 µg recombinant follicle stimulating hormone (FSH) per day. For example, the composition may be for administration at doses of 12 µg recombinant FSH every day, or less typically at an equivalent of 36 µg recombinant FSH every three days (e.g., for administration on days 1, 4, 7 and so on). For example, the composition is for administration at a dose of 12 µg recombinant FSH per day. Also provided are methods of treating infertility in a patient in need thereof of (e.g., identified as being of) ages≤35 years, comprising administering to the patient recombinant follicle stimulating hormone (rFSH) at a dose of, or a dose equivalent to, 12 µg recombinant FSH per day.

As noted above, the administration of recombinant FSH starts on day one of treatment and may continue for two to twenty days. As noted above, the dose may be the same every day. However, variation of the dose e.g., depending on the patient's ovarian response (e.g., depending on follicular growth, e.g., as measured by ultrasonography) is more likely.

As noted above, the recombinant FSH composition (e.g., pharmaceutical composition) or medicament may be administered after pre-treatment of the patient with a (different) pharmaceutical composition, herein termed "composition A", which suppresses endogenous gonadotropin production prior to day one of the treatment with FSH, such as a steroid, a GnRH agonist, a GnRH antagonist etc.

As noted above, typically the recombinant FSH composition (e.g., pharmaceutical composition) or medicament is for administration prior to administration of a high (ovulatory) dose of hCG (for example 4,000 to 11,000 IU hCG, e.g., 5,000 IU hCG, 10,000 IU hCG etc.; or 150 to 500 μg recombinant hCG, for example 250 μg recombinant hCG) to induce final follicular maturation. In some embodiments, the methods described herein further comprise administration of a high (ovulatory) dose of human chorionic gonadotropin (hCG).

As noted above, the treatment of infertility may further comprise: retrieving (e.g., harvesting) oocyte(s); fertilizing (e.g., inseminating) the oocytes (s); and allowing the fertilized oocytes to develop to the blastocyst stage. As noted above, the treatment of infertility may further comprise assessing the quality of blastocysts and fresh transfer of blastocyst(s) or freezing of blastocysts for later transfer.

As noted above, the treatment may further comprise monitoring and/or control of over-response to treatment (e.g., OHSS).

In a further aspect there are provided methods of treating infertility in a patient of ages≤34 years and a composition comprising recombinant follicle stimulating hormone (FSH) for use in the treatment of infertility in a patient of ages≤34 years, wherein the methods comprise, and composition is for, administration at a starting dose of 12 μg recombinant FSH per day, wherein the starting dose is administered on at least day 1 of treatment (including on at least day 1 and day 2 of treatment, including on each of days 1 to 4 of treatment), optionally wherein the dose is (i) increased by a first incremental dose increase of 2 to 4 μg rFSH (including 3 μg rFSH) on any subsequent day of treatment; and/or (ii) decreased by a first incremental dose decrease of 2 to 4 μg rFSH (including 3 μg rFSH) on any subsequent day of treatment.

The dose may be maintained at the starting dose for the duration of the treatment. However, variation of the dose e.g., depending on the patient's ovarian response (e.g., depending on follicular growth e.g., as measured by ultrasonography)) is more likely.

The method of treating infertility may include monitoring the patient's ovarian response to administration of rFSH (e.g., monitoring follicular growth, e.g., as measured by ultrasonography). The method of treating infertility may include monitoring the patient's ovarian response to administration of rFSH (e.g., a step of monitoring follicular growth, e.g., as measured by ultrasonography) and, depending on follicular growth (e.g., as measured by ultrasonography), increasing or decreasing the dose by 2 to 4 μg rFSH (including 3 μg rFSH). The method of treating infertility may include monitoring the patient's ovarian response to administration of rFSH (e.g., a step of monitoring follicular growth, e.g., as measured by ultrasonography) on one or more days throughout the course of treatment, such as on one or more of day 5, day 7, day 9, day 11, day 13, day 15, day 17 and day 19 of treatment. The method of treating infertility may include monitoring the patient's ovarian response to administration of rFSH (e.g., monitoring follicular growth, e.g., as measured by ultrasonography) on one or more days throughout the course of treatment, such as on one or more of day 5, day 7, day 9, day 11, day 13, day 15, day 17 and day 19 of treatment, and, depending on follicular growth (e.g., as measured by ultrasonography), increasing or decreasing the dose by 2 to 4 μg rFSH (including 3 μg rFSH). That is, the dose may be increased or decreased depending on follicular growth on one or more days throughout the course of treatment, such as on one or more of day 5, day 7, day 9, day 11, day 13, day 15, day 17 and day 19 of treatment.

The dose may be increased in increments during treatment, decreased in increments during treatment, or be varied during treatment by both incremental dose increases and incremental dose decreases. Typically, dose increases are not implemented more frequently than once every 2 days; that is, a second incremental dose increase is not implemented until at least two days after a first incremental dose increase. This gradual increase constitutes a safe approach, and permits the treating physician to assess ovarian response to a given dose level before possibly increasing the dose. Dose decreases may be implemented as frequently as every day. For example, the treating physician may decrease the dose for subjects with follicular growth indicating that a dose reduction would be an appropriate course of action. The dose may be increased to a maximum daily dose of 24 μg rFSH or decreased to a minimum daily dose of 6 μg rFSH.

Thus, a first incremental dose increase of 2 to 4 μg FSH (including 3 μg rFSH) may be (a) followed by a further incremental dose increase of 2 to 4 μg rFSH (including 3 μg rFSH) at least two days after the previous incremental increase in dose; and/or (b) followed by at least one incremental dose decrease of 2 to 4 μg rFSH (including 3 μg FSH) at least one day after the previous incremental increase in dose. A first incremental dose decrease of 2 to 4 μg rFSH (including 3 μg rFSH) may be (a) followed by an incremental dose increase of 2 to 4 μg rFSH (including 3 μg rFSH) at least one day, or at least two days, after the previous incremental decrease in dose; and/or (b) followed by a further incremental dose decrease of 2 to 4 μg rFSH (including 3 μg rFSH) at least one day after the previous decrease in dose.

It will be appreciated that this aspect contemplates, for example, a starting dose of 12 μg recombinant FSH per day from day 1 of treatment to day 4 of treatment, the dose being increased in subsequent days of treatment by at least one increment of, e.g., 3 μg rFSH to 15 μg rFSH (e.g., on day 5 or 6). The dose of 15 μg rFSH may be continued to the end of treatment, or there may be 1-3 further incremental dose increases of, e.g., 3 μg rFSH (e.g., to 18 μg; to 18 μg and then to 21 μg rFSH; or to 18 μg, to 21 μg and then to the maximum dose of 24 μg rFSH) with each incremental dose increase being at least two days after the previous incremental dose increase, or the dose being varied by both incremental dose increases and incremental dose decreases, each at the appropriate interval after the previous incremental dose change, as may be warranted in view of the patient's ovarian response, as discussed above. Similarly, an initial dose reduction of, e.g., 3 μg rFSH to 9 μg rFSH (e.g., on day 5 or 6) may be continued to the end of treatment, or there may be one further incremental dose decrease of, e.g., 3 μg FSH (e.g., to the minimum dose of 6 μg rFSH), with each incremental dose decrease at least one day after the previous incremental dose decrease, or the dose being varied by both incremental dose increases and incremental dose decreases, each at the appropriate interval after the previous incremental dose change, as may be warranted in view of the patient's ovarian response, as discussed above. This aspect of the invention provides a means of varying the FSH dose in a safe manner based on the patient's response.

As with the first aspect discussed above, treatment in accordance with this aspect may further comprise administration of a high (ovulatory) dose of human chorionic gonadotropin (hCG), and, optionally, retrieving (e.g., harvesting) oocyte(s); fertilizing (e.g., inseminating) the oocytes (s); allowing the fertilized oocytes to develop to the blastocyst stage, further optionally assessing the quality of blastocysts and fresh transfer of blastocyst(s) or freezing of blastocysts for later transfer. Additionally or alternatively, the treatment may further comprise monitoring and/or control of over-response to treatment (e.g., OHSS).

Recombinant FSH and rFSH Compositions

As noted above, the methods and compositions described herein use recombinant FSH (rFSH). FSH comprises a 92 amino acid alpha sub-unit, also common to the other glycoprotein hormones LH and chorionic gonadotropin (CG), and a 111 amino acid beta sub-unit unique to FSH that confers the biological specificity of the hormone (Pierce and Parsons, 1981). Each sub-unit is post translationally modified by the addition of complex carbohydrate residues. Both sub-units carry 2 sites for N-linked glycan attachment, the alpha sub-unit at amino acids 52 and 78 and the beta sub-unit at amino acid residues 7 and 24 (Rathnam and Saxena, 1975, Saxena and Rathnam, 1976). FSH is thus glycosylated to about 30% by mass (Dias and Van Roey. 2001. Fox et al. 2001).

The glycosylation of rFSH products reflects the range of glycosyl-transferases present in the host cell line. Commercially available rFSH products derived from engineered CHO cells have a more limited range of glycan modifications than those found on the natural products. Examples of the reduced glycan heterogeneity found in CHO cell derived rFSH include a lack of bisecting glucosamine and a reduced content of core fucosylation and acetyl lactosamine extensions (Hard et al., 1990). In addition, CHO cells are only able to add sialic acid using the α2,3 linkage (Kagawa et al, 1988, Takeuchi et al, 1988, Svensson et al., 1990); CHO cell-derived rFSH only includes α2,3-linked sialic acid and does not include α2,6-linked sialic acid. Thus, CHO cell-derived rFSH is different from naturally produced FSH (e.g., human pituitary/serum/urinary FSH) which contains glycans with a mixture of α2,3 and α2,6-linked sialic acid, with a predominance of the former.

As noted above, the present applicants have developed a human cell line-derived rFSH which is the subject of International Patent Application No. PCT/GB2009/000978, published as WO2009/127826A, and also approved by the EC as REVOKELLE® (follitropin delta, also known as FE 999049). Recombinant FSH with a mixture of both α2,3 and α2,6-linked sialic acid was made by engineering a human cell line to express both rFSH and α2,3 sialyltransferase. The amino acid sequence of the human cell line-derived recombinant FSH which is the subject of International Patent Application No. PCT/GB2009/000978, published as WO2009/127826A (e.g., FE 999049), is the native human FSH sequence, but the product has a different glycosylation pattern. The expressed product is highly acidic and carries a mix of both α2,3- and α2,6-linked sialic acids; the latter provided by the endogenous sialyl transferase activity. It was found that the type of sialic acid linkage, α2,3- or α2,6-, can have a dramatic influence on biological clearance of FSH. Thus REVOKELLE® (e.g., FE 999049) may be more biologically appropriate compared to CHO cell-derived recombinant products that have only α2,3 linked sialic acid (Kagawa et al, 1988, Takeuchi et al, 1988, Svensson et al., 1990) and have decreased sialic acid content (Ulloa-Aguirre et al. 1995, Andersen et al. 2004).

Thus, the recombinant FSH used in accordance with the methods and compositions described herein may be produced or expressed in a human cell line, such as a PER.C6® cell line. The recombinant FSH may be produced or expressed in a PER.C6® cell line, a PER.C6® derived cell line or a modified PER.C6® cell line. Recombinant FSH which is produced or expressed in a PER.C6® cell line will include some α2,6-linked sialic acids (α2,6 sialylation) provided by endogenous sialyl transferase activity (of the cell line) and will include some α2,3-linked sialic acids (α2,3 sialylation) provided by endogenous sialyl transferase activity. The cell line may be modified using α2,3-sialyltransferase. The cell line may be modified using α2,6-sialyltransferase. Alternatively or additionally, the recombinant FSH may include α2,6-linked sialic acids (α2,6 sialylation) provided by endogenous sialyl transferase activity (of the cell line). Herein, the term "human-derived recombinant FSH" means recombinant FSH which is produced or expressed in a human cell line (e.g., recombinant FSH made by engineering a human cell line).

The recombinant FSH used in the methods and compositions described herein may include α2,3- and α2,6-sialylation. The recombinant FSH for use according to the invention may have 1% to 99% of the total sialylation being α2,3-sialylation. The recombinant FSH for use according to the invention may have 1% to 99% of the total sialylation being α2,6-sialylation. The recombinant FSH may have 1% to 50% of the total sialylation as α2, 6-sialyation, and 50% to 99% of the total sialylation as 2,3-sialyation. For example, 80% to 95%, for example 80% to 90%, for example 82% to 89%, for example 85% to 89% of the total sialylation may be α2,3-sialylation. For example, 5% to 20%, for example 10% to 20%, for example 11% to 18%, for example 11% to 15%, of the total sialylation may be α2,6-sialylation. In an example, the recombinant FSH has 5% to 20% of the total sialylation as α2, 6-sialyation, and 80% to 95% of the total sialylation as 2,3-sialyation. In another example, the recombinant FSH has 50% to 80% of the total sialylation as α2, 6-sialyation, and 20% to 50% of the total sialylation as 2,3-sialyation.

Herein, by "sialylation", it is meant the amount of sialic residues present on the recombinant FSH carbohydrate structures. Consistent with usage in the art, α2,3-sialylation means sialylation at the 2,3 position and α2,6 sialylation means sialylation at the 2,6 position. Thus "% of the total sialylation may be a 2,3 sialylation" refers to the % of the total number of sialic acid residues present in the FSH (or hCG) which are sialylated in the 2,3 position. The term "% of the total sialylation being α2,6-sialylation" refers to the % of the total number of sialic acid residues present in the FSH (or hCG) which are sialylated in the 2,6 position.

In all aspects, the rFSH may be present as a single isoform or as a mixture of isoforms.

The composition may be a pharmaceutical composition. The pharmaceutical composition is for the treatment of infertility. The treatment of infertility may comprise COS prior to ART. The pharmaceutical composition may be used, for example, in medical indications where known FSH preparations are used, in accordance with the methods and treatment protocols disclosed herein The recombinant FSH, composition, or pharmaceutical composition can be formulated into well-known compositions for any route of drug administration, e.g., oral, rectal, parenteral, transdermal (e.g., patch technology), intravenous, intramuscular, subcutaneous (e.g., for subcutaneous injection), intracisternal, intravaginal, intraperitoneal, local (powders, ointments or drops) or as a buccal or nasal spray. A typical composition comprises a pharmaceutically acceptable carrier, such as aqueous solution, nontoxic excipients, including salts and preservatives, buffers and the like, as described in Remington's Pharmaceutical Sciences fifteenth edition (Matt Publishing Company, 1975), at pages 1405 to 1412 and 1461-87, and the national formulary XIV fourteenth edition (American Pharmaceutical Association, 1975), among others. For example, the recombinant FSH, composition or pharmaceutical composition can be formulated for injection, such as for subcutaneous injection.

Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate.

The compositions of the present invention may also comprise additives such as but not limited to preservatives, wetting agents, emulsifying agents, surfactants and dispersing agents. Antibacterial and antifungal agents can be included to prevent growth of microbes and includes, for example, m-cresol, benzyl alcohol, paraben, chlorobutanol, phenol, sorbic acid, and the like. If a preservative is included, benzyl alcohol, phenol and/or m-cresol are preferred; however, the preservative is by no means limited to these examples. Furthermore, it may be desirable to include isotonic agents such as sugars, sodium chloride, amino acids and the like.

For example, the composition or medicament may comprise recombinant FSH and one or more of polysorbate 20, L-methionine, phenol, and arginine hydrochloride. Such a composition may be formulated for injection, such as for subcutaneous injection. For example, the composition or medicament may be the REKOVELLE® formulation (rFSH with excipients phenol, polysorbate 20, L-methionine, sodium sulphate decahydrate, disodium phosphate dodecahydrate, phosphoric acid [concentrated, for pH-adjustment], sodium hydroxide [for pH-adjustment], and water for injection).

Injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Injectable formulations can be supplied in any suitable container, e.g., vial, pre-filled syringe, injection cartridges, and the like.

The recombinant FSH, composition, or medicament may be formulated for single use or for multiple use (multiple dose). If the recombinant FSH, composition, or medicament is formulated for multiple use, typically one or more preservatives is included. If a preservative is included, benzyl alcohol, phenol or m-cresol, are preferred; however, the preservative is by no means limited to these examples. The single use or multiple use formulated composition or medicament may further comprise an amino acid or combination of amino acids. Typically, the amino acid is arginine, for example added as arginine or more typically arginine hydrochloride.

The recombinant FSH, composition, or medicament may be included in a container such as a vial, prefilled cartridge (e.g., for single administration or multiple use) or an injection device such as a "pen" for e.g., administration of multiple doses.

The recombinant FSH, composition or pharmaceutical composition may be a formulation (e.g., injectable formulation) including rFSH.

The recombinant FSH, composition or medicament can be supplied in any appropriate package. For example, a composition or medicament can include a number of containers (e.g., pre-filled syringes or vials) containing FSH. The syringes or vials may be packaged in a blister package or other means to maintain sterility. Any composition or medicament can optionally include instructions for using the FSH formulation.

The pH and exact concentration of the various components of the pharmaceutical composition are adjusted in accordance with routine practice in this field. See GOODMAN and GILMAN's THE PHARMACOLOGICAL BASIS FOR THERAPEUTICES, $7^{th}$ ed. In a typical embodiment, the recombinant FSH, composition or medicament are supplied as compositions for parenteral administration. General methods for the preparation of the parenteral formulations are known in the art and are described in REMINGTON; THE SCIENCE AND PRACTICE OF PHARMACY, supra, at pages 780-820. The parenteral compositions can be supplied in liquid formulation or as a solid which will be mixed with a sterile injectable medium just prior to administration. The parenteral compositions may be supplied in dosage unit form for ease of administration and uniformity of dosage.

In a further aspect there is provided the use of recombinant follicle stimulating hormone (FSH) in the manufacture of a medicament for use in the treatment of infertility in a patient of (e.g., identified as being of) age≥35 years as described herein.

In a further aspect there is provided the use of recombinant follicle stimulating hormone (FSH) in the manufacture of a medicament for use in the treatment of infertility in a patient identified as being of ages≤34 years as described herein.

Further aspects are illustrated in the following examples, which are not limiting in any respect.

EXAMPLES

Example 1: A Randomized, Double-Blind, Placebo-Controlled, Parallel Groups, Multicenter Trial Investigating the Efficacy and Safety of FE 999049 (Rekovelle®) in Controlled Ovarian Stimulation in Women Aged 35-42 Years Undergoing Assisted Reproductive Technology Dose Selection Dose selection was informed by a prior clinical trial by the applicants that did not consider age as a factor for dose selection. In particular, a phase 2 dose-response trial for FE 999049 was conducted in 265 IVF/ICSI patients aged up to 37 years old. It evaluated ovarian response to five different doses of FE 999049 (5.2, 6.9, 8.6, 10.3, and 12.1 µg; fixed dose) along with 150 IU GONAL-F which was included as reference treatment. The primary endpoint was the number of oocytes retrieved. A statistically significant ($p<0.001$) dose-response was established for FE 999049 with respect to number of oocytes retrieved for the tested dose range 5.2-12.1 µg. A dose-response relationship was also seen for follicular volume, estradiol, inhibin B and inhibin A at the end of stimulation (all $p<0.001$). At the subject level, the proportion of women with ≥15 oocytes retrieved increased with increasing FE 999049 dose. The FE 999049 dose level of 12.1 µg FE 999049 yielded the highest mean number of oocytes, proportion of women with ≥15 oocytes retrieved, the lowest proportion of patients with <3 oocytes retrieved, and the highest number of fertilized oocytes.

Modelling of OHSS risk was not feasible based on the phase 2 data due to the relatively low event rate. However, the incidence of OHSS is correlated with the extent of ovarian response and thereby indirectly addressed in these analyses. In the phase 2 trial, early moderate OHSS occurred only at the 10.3 and 12.1 µg FE 999049 doses (one subject in each group). Concerning other safety aspects, the overall incidence of adverse events with 12.1 µg FE 999049 was not higher than that observed with 10.3 µg in the phase 2 trial.

Based on the above rationale, a starting dose of 12 µg FE 999049 is proposed by the present applicants for the age group of <35 years old (e.g., ages≤34 years) ART patients, e.g., IVF/ICSI patients (see Example 2 below).

A retrospective internal analysis of unpublished data for subjects with age≥35 years who after stimulation with 12 µg FE 999049 in the trial described above had 4-7 oocytes retrieved were assigned a 25% dose increase in a second cycle trial. As shown in the table below, the dose increase from 12 µg to 15 µg FE 999049 was associated with an average increase of 1.2 oocytes and 1.2 fertilized oocytes, without an accompanying increase in the incidence of moderate/severe OHSS. These data suggest to the applicants that some women ≥35 years of age may benefit from receiving 15 µg rather than 12 µg FE 999049 with no safety concerns. In these older women treated with a moderately higher starting dose of 15 µg, excessive response can be managed by GnRH agonist triggering without compromising cumulative efficacy outcome.

Ovarian Response in Subjects ≥35 Years Treated with 12 µg FE 999049 in Cycle 1 and 15 µg FE 999049 in Cycle 2

|  | Cycle 1<br>12 µg FE 999049 | Cycle 2<br>15 µg FE 999049 |
| --- | --- | --- |
| Oocytes retrieved | 5.5 (1.0) | 6.7 (4.0) |
| Fertilized oocytes | 2.6 (1.3) | 3.8 (2.5) |
| Moderate/severe OHSS | 0% | 0% |

Data are mean (SD) or percentage.
N = 34

In conclusion, the first trial discussed above establishes to the applicants that a safe and effective starting dose is 12 µg FE 999049 for women <35 years of age (e.g., ages≤34 years), and the retrospective analysis discussed above suggests to the applicants that a safe and effective a starting dose is 15 µg FE 999049 for older women, e.g., 35-42 years old.

In the treatment of women age≥35 years described herein, dose increases are allowed in a gradual manner, with the starting dose of 15 µg being fixed for the first four days, and later dose increases to be done not more frequently than once every 2 days. This gradual increase constitutes a safe approach with the investigator judging the ovarian response to a dose level before possibly increasing the dose. Decreases in daily FE 999049 dose during the stimulation period will be implemented per the investigator's judgement, such as for subjects with follicular growth indicating that a dose reduction would be an appropriate course of action.

It is expected by the applicants that the trial will show that the dosing protocol will maximize both oocyte yield and resultant cumulative pregnancy rates while maintaining safety.

The protocol also provides a composition for treatment of patients with high response through use of a GnRH agonist trigger and cryopreserved embryo transfer-only cycles for those patients.

Methodology

This will be a randomized, double-blind, placebo-controlled, parallel groups, multicenter trial assessing the efficacy and safety of the recombinant FSH preparation FE 999049 in subjects aged 35-42 years undergoing controlled ovarian stimulation for IVF/ICSI following a gonadotropin-releasing hormone (GnRH) antagonist protocol. The primary endpoint is the cumulative ongoing pregnancy rate after the fresh cycle and cryopreserved cycles initiated within 12 months from the start of controlled ovarian stimulation. Thereby, the trial is designed to capture the clinical efficacy of a single controlled ovarian stimulation cycle in a more complete manner by following outcomes from both the fresh and subsequent cryopreserved cycles. Secondary endpoints include pharmacodynamic parameters of FSH action as well as efficacy and safety parameters related to controlled ovarian stimulation from the fresh cycle and subsequent cryopreserved cycles.

Controlled Ovarian Stimulation and Fresh Cycle

Subjects will be screened within 90 days prior to randomization for compliance with the inclusion and exclusion criteria (see below). On day 2-3 of the menstrual cycle, subjects will be randomized in a 10:1 ratio to FE 999049 or placebo, and controlled ovarian stimulation will be initiated. FE 999049 and placebo will be self-administered subcutaneously using a pre-filled injection pen.

Subjects assigned to treatment with FE 999049 will receive a starting dose of 15 µg daily that is fixed for the first four stimulation days. Based on ovarian response, the dose may be adjusted by 3 µg, with dose increases implemented not more frequently than once every 2 days and/or dose decreases implemented per investigator's judgement. The minimum daily dose is 6 µg, and the maximum daily dose is 24 µg. Subjects assigned to placebo will have the injection pen dialed to the same value (dose) as if administered FE 999049. Subjects can be treated with FE 999049 or placebo for a maximum of 20 days. Coasting, use of dopamine agonist or any other drug to prevent early ovarian hyperstimulation syndrome (OHSS) with the exception of GnRH agonist for triggering of final follicular maturation, are not allowed.

During stimulation, subjects will be monitored by transvaginal ultrasound on stimulation days 1 and 5 and thereafter at least every second day. When the leading follicle reaches a diameter of ≥14 mm, transvaginal ultrasound will be performed daily. To prevent a premature luteinizing hormone (LH) surge, 250 µg GnRH antagonist (ganirelix acetate, GANIRELIX®, Merck Sharp & Dohme) will be initiated on stimulation day 5 for subjects with ≥3 follicles with a diameter of ≥10 mm. Subjects who fail to satisfy this GnRH antagonist criterion on stimulation day 5 will continue to be monitored at least every second day, and GnRH antagonist will be initiated when/if the criterion is met. The GnRH antagonist will be continued throughout the stimulation period. Triggering of final follicular maturation will be done as soon as ≥2 follicles with a diameter of ≥17 mm are observed. If there are <20 follicles with a diameter of ≥12 mm, 10,000 IU human chorionic gonadotropin (hCG; NOVAREL®, Ferring Pharmaceuticals) will be administered. If there are ≥20 follicles with a diameter of ≥12 mm or the serum estradiol concentration is ≤3,000 µg/mL (blood test well known in the art), 4.0 mg GnRH agonist (leuprolide acetate, LEUPROLIDE ACETATE®, Sandoz) will be administered, and the fresh blastocyst transfer will be cancelled. If after 8 days of stimulation, the investigator judges that the triggering criterion is not likely to be reached by day 20, the cycle will be cancelled. If the triggering criterion is not met after 20 days of stimulation, the cycle will be cancelled.

Oocyte retrieval will take place 36 h (±2 h) after triggering of final follicular maturation, and oocytes will be inseminated by IVF or ICSI 4 h (±1 h) after retrieval. Rescue ICSI (Intracytoplasmic sperm injection) is not allowed. Fertilization and embryo development will be assessed. For subjects who undergo triggering of final follicular maturation with hCG and have <20 oocytes retrieved, transfer will be performed on day 5 (blastocyst stage) after oocyte retrieval. Assessment of blastocyst quality on day 5 after oocyte retrieval will be assess of three parameters: blastocyst expansion and hatching status (grade 1-6), blastocyst inner cell mass grading (grade A-D) and trophectoderm grading (grade A-D) as is well known in the art. Blastocysts will be given a numerical score by using the system of Gardner & Schoolcraft, as is well known in the art, with the addition of D-categories for inner cell mass and trophectoderm. Subjects will have one blastocyst transferred if at least one good-quality (i.e. grade 3BB or above) blastocyst is available, or one or two blastocysts transferred if no good-quality blastocyst is available. Remaining blastocysts will be cryopreserved by vitrification. For subjects with ≥20 oocytes retrieved following hCG administration and for subjects who undergo triggering of final follicular maturation with GnRH agonist, no transfer will take place in the fresh cycle and blastocysts will instead be cryopreserved.

A subject who fails to reach the triggering criterion due to poor ovarian response or who has ≤3 oocytes retrieved will be offered medication and financial support for an ART cycle with an approved gonadotropin preparation outside of the trial.

Vaginal progesterone inserts (progesterone, ENDOMETRIN®, Ferring Pharmaceuticals) 100 mg three times daily (TID) will be provided for luteal phase support from the day after oocyte retrieval and continuing until menses, negative β human chorionic gonadotropin (βhCG test), pregnancy loss or until ongoing pregnancy has been documented.

A serum βhCG test will be performed 10-14 days after transfer, clinical and vital pregnancy will be confirmed by transvaginal ultrasound 5-6 weeks after transfer, and ongoing pregnancy will be confirmed by transvaginal or abdominal ultrasound 8-9 weeks after transfer.

Cryopreserved Cycles

The trial covers cryopreserved cycles initiated within 12 months from the start of controlled ovarian stimulation. Either a programmed or natural cycle can be selected for any cryopreserved cycle.

Any programmed cryopreserved cycle will be initiated within 3 days of start of menses with administration of estradiol (ESTRADIOL Tablets USP, Teva Pharmaceuticals USA, Inc.) 2 mg TID or 3 mg two times daily (BID) (or 3 mg TID at the investigator's discretion, if a daily dose of 6 mg has been shown to be insufficient in a previous cycle). If after 10-12 days of estradiol treatment the endometrial thickness is ≥8 mm, the subject will initiate daily intramuscular (IM) injections of 50 mg progesterone (PROGESTERONE Injection USP, West-ward Pharmaceutical Corp or Watson Pharma, Inc.) within the next 5 days in conjunction with the estradiol treatment. The ultrasound evaluation can be repeated within 7 days if the endometrial thickness criterion is not met. In programmed cryopreserved cycles, transfer of one or two blastocysts will occur on the 6$^{th}$ day from start of progesterone after warming and assessment of blastocyst survival and re-expansion. Subjects will have one blastocyst transferred if at least one good-quality (i.e. grade 3BB or above) blastocyst is available, or one or two blastocysts transferred if no good-quality blastocyst is available. Luteal phase support (estradiol and IM progesterone) will continue to be administered until menses, negative βhCG test, pregnancy loss or until ongoing pregnancy has been documented.

Any natural cryopreserved cycle will be initiated 7 days after start of menses with monitoring of urinary LH on a daily basis by the subject. The day after confirmation of LH surge by serum LH (local laboratory) and endometrial thickness of ≥8 mm, the subject will start luteal phase support with vaginal progesterone inserts (progesterone, ENDOMETRIN®, Ferring Pharmaceuticals) 100 mg TID. In a natural cryopreserved cycle, transfer of one or two blastocysts will occur on day LH surge +7 after warming and assessment of blastocyst survival and re-expansion. Subjects will have one blastocyst transferred if at least one good-quality (i.e. grade 3BB or above) blastocyst is available, or one or two blastocysts transferred if no good-quality blastocyst is available. Luteal phase support (vaginal progesterone) will continue to be administered until menses, negative βhCG test, pregnancy loss or until ongoing pregnancy has been documented.

Failure to achieve endometrial thickness ≥8 mm in the first cryopreserved cycle will result in cycle cancellation, and in the programmed cycles, administration of 100 mg IM progesterone (PROGESTERONE Injection USP, West-ward Pharmaceutical Corp or Watson Pharma, Inc.) to induce withdrawal bleeding. In subsequent cryopreserved cycles, blastocyst transfer can take place regardless of endometrial thickness at the investigator's discretion.

In both programmed and natural cryopreserved cycles, a serum βhCG test is performed 10-14 days after transfer, clinical and vital pregnancy will be confirmed by transvaginal ultrasound 5-6 weeks after transfer, and ongoing pregnancy will be confirmed by transvaginal or abdominal ultrasound 8-9 weeks after transfer.

After completion of the trial, the subject is allowed to use cryopreserved blastocysts in accordance with local guidelines and/or regulations.

All subjects with an ongoing pregnancy obtained in the fresh cycle or in cryopreserved cycles initiated within 12 months from the start of controlled ovarian stimulation will be followed until delivery to collect information on live birth rate. Furthermore, data will be collected on neonatal health, including minor/major congenital anomalies, at birth, 4 weeks and 1 year after birth.

Inclusion Criteria

1. Informed Consent Documents signed prior to any trial-related procedure.
2. In good physical and mental health in the judgement of the investigator.
3. Pre-menopausal females between the ages of 35 and 42 years. The subjects must be at least 35 years (including the 35$^{th}$ birthday) when they sign the informed consent and no more than 42 years (up to the day before the 43$^{rd}$ birthday) at the time of randomization.
4. Body mass index (BMI) between 17.5 and 38.0 kg/m$^2$ (both inclusive) at screening.
5. Infertile women diagnosed with tubal infertility, unexplained infertility, endometriosis stage I/II or with partners diagnosed with male factor infertility, eligible for in vitro fertilization (IVF) and/or intracytoplasmic sperm injection (ICSI) using fresh or frozen ejaculated sperm from male partner or sperm donor.
6. Documented history of infertility for at least 6 months before randomization (not applicable in case of tubal or severe male factor infertility, or when the use of donor sperm is indicated).
7. Regular menstrual cycles of 24-35 days (both inclusive).
8. Hysterosalpingography, hysteroscopy or saline infusion sonography, documenting a uterus consistent with expected normal function (e.g. no evidence of clinically interfering uterine fibroids defined as submucous fibroids of any size or intramural fibroids larger than 3 cm in diameter, no polyps and no congenital structural abnormalities which are associated with a reduced chance of pregnancy) at screening or within 1 year prior to screening.
9. Transvaginal ultrasound documenting presence and adequate visualization of both ovaries, without evidence of significant abnormality (e.g. enlarged ovaries which would contraindicate the use of gonadotropins) and normal adnexa (e.g. no hydrosalpinx) at screening. Both ovaries must be accessible for oocyte retrieval.
10. Early follicular phase (cycle day 2-4) serum levels of follicle-stimulating hormone (FSH) between 1 and 15 IU/L (results obtained within 3 months prior to randomization).
11. Negative serum Hepatitis B Surface Antigen (HBsAg), Hepatitis C Virus (HCV) and Human Immunodeficiency Virus (HIV) antibody tests at screening or within 6 months prior to screening.
12. Willing to accept the blastocyst transfer policy for the fresh cycle and the cryopreserved cycles initiated within 12 months from the start of controlled ovarian stimulation using blastocysts obtained in this trial, i.e. transfer of one blastocyst (if a good-quality blastocyst is available) or transfer of one or two blastocysts (if no good-quality blastocyst is available).
13. Willing and able to comply with trial procedures, including filling in the diary and attending scheduled visits as well as providing the neonatal health data up to 1 year after birth.

Exclusion Criteria
1. More than one previous controlled ovarian stimulation cycle for IVF/ICSI.
2. Known endometriosis stage III-IV (defined by the revised American Society for Reproductive Medicine (ASRM) classification, 2012).
3. Known history of anovulation.
4. One or more follicles ≥10 mm (including cysts) observed on the transvaginal ultrasound prior to randomization on stimulation day 1.
5. Known history of recurrent miscarriage (defined as three consecutive losses after ultrasound confirmation of pregnancy [excl. ectopic pregnancy] and before week 24 of pregnancy).
6. Known abnormal karyotype of subject or of her partner/sperm donor, as applicable, depending on source of sperm used for insemination in this trial. In case partner sperm will be used and the sperm production is severely impaired (concentration <1 million/mL), normal karyotype, including no Y-chromosome microdeletion, must be documented.
7. Any known clinically significant systemic disease (e.g. insulin-dependent diabetes).
8. Known inherited or acquired thrombophilia.
9. Active arterial or venous thromboembolism or severe thrombophlebitis, or a history of these events.
10. Any known endocrine or metabolic abnormalities (pituitary, adrenal, pancreas, liver or kidney) with the exception of pharmacologically controlled sub-clinical hypothyroidism.
11. Known tumors of the ovary, breast, uterus, adrenal gland, pituitary or hypothalamus which would contraindicate the use of gonadotropins.
12. Known moderate or severe impairment of renal or hepatic function.
13. Any abnormal finding of clinical chemistry, hematology, thyroid-stimulating hormone (TSH) or prolactin, or vital signs at screening, which is judged clinically significant by the investigator.
14. Currently breast-feeding.
15. Undiagnosed vaginal bleeding.
16. Known abnormal cervical cytology of clinical significance observed within three years prior to randomization (unless the clinical significance has been resolved).
17. Findings at the gynecological examination at screening which preclude gonadotropin stimulation or are associated with a reduced chance of pregnancy, e.g. congenital uterine abnormalities or retained intrauterine device.
18. Pregnancy (negative urinary pregnancy tests must be documented at screening and prior to randomization) or contraindication to pregnancy.
19. Known current active pelvic inflammatory disease.
20. Use of fertility modifiers during the last menstrual cycle before randomization, including dehydroepiandrosterone (DHEA), metformin or cycle programming with oral contraceptives, progestogen or estrogen preparations.
21. Use of hormonal preparations (except for thyroid medication) during the last menstrual cycle before randomization.
22. Known history of chemotherapy (except for gestational conditions) or radiotherapy.
23. Current or past (1 year prior to randomization) abuse of alcohol or drugs.
24. Current (last month) intake of more than 14 units of alcohol per week (one unit is equivalent to 12 fluid ounces of regular beer (5% alcohol), 5 fluid ounces of wine (12% alcohol), or 1.5 fluid ounces of 80 proof distilled spirits (40% alcohol).
25. Current or past (3 months prior to randomization) smoking habit of more than 10 cigarettes per day.
26. Known hypersensitivity to any active ingredient or excipients in the medicinal products used in this trial.
27. Any known clinical condition that would prevent the use of estrogen or progestin compounds.
28. Previous participation in this trial.
29. Use of any non-registered investigational drugs during the last 3 months prior to randomization.

Example 2: A Randomized, Double-Blind, Placebo-Controlled, Parallel Groups, Multicenter Trial Investigating the Efficacy and Safety of FE 999049 in Controlled Ovarian Stimulation in Women Aged 18-34 Years Undergoing Assisted Reproductive Technology Dose Selection The rationale behind the selection of 12 µg FSH for this patient population is explained in the "dose selection" part of Example 1. It is expected by the applicants that the trial will show that the dosing protocol will maximize both oocyte yield and resultant cumulative pregnancy rates while maintaining safety. The protocol also provides a composition for treatment of patients with high response through use of a GnRH agonist trigger and cryopreserved embryo transfer-only cycles for those patients.

Methodology

This will be a randomized, double-blind, placebo-controlled, parallel groups, multicenter trial assessing the efficacy and safety of the rFSH preparation FE 999049 in subjects aged 18-34 years undergoing controlled ovarian stimulation for IVF/ICSI following a gonadotropin-releasing hormone (GnRH) antagonist protocol. The primary endpoint is the cumulative ongoing pregnancy rate after the fresh cycle and cryopreserved cycles initiated within 12 months from the start of controlled ovarian stimulation. Thereby, the trial is designed to capture the clinical efficacy of a single controlled ovarian stimulation cycle in a more complete manner by following outcomes from both the fresh and subsequent cryopreserved cycles. Secondary endpoints include pharmacodynamic parameters of FSH action as well as efficacy and safety parameters related to controlled ovarian stimulation from the fresh cycle and subsequent cryopreserved cycles.

Controlled Ovarian Stimulation and Fresh Cycle

Subjects will be screened within 90 days prior to randomization for compliance with the inclusion and exclusion criteria. These criteria are similar to Example 1, with the exception of the inclusion criterion 3: in this Example 2 trial the patients are pre-menopausal females between the ages of 18 and 34 years. The subjects must be at least 18 years (including the $18^{th}$ birthday) when they sign the informed consent and no more than 34 years (up to the day before the $35^{th}$ birthday) at the time of randomization. On day 2-3 of the menstrual cycle, subjects will be randomized in a 10:1 ratio to FE 999049 or placebo, and controlled ovarian stimulation will be initiated. FE 999049 and placebo will be self-administered subcutaneously using a pre-filled injection pen.

Subjects assigned to treatment with FE 999049 will receive a starting dose of 12 μg daily that is fixed for the first four stimulation days. Based on ovarian response, the dose may be adjusted by 3 μg, with dose increases implemented not more frequently than once every 2 days and/or dose decreases implemented per investigator's judgement. The minimum daily dose is 6 μg, and the maximum daily dose is 24 μg. Subjects assigned to placebo will have the injection pen dialed to the same value (dose) as if administered FE 999049. Subjects can be treated with FE 999049 or placebo for a maximum of 20 days. Coasting, use of dopamine agonist or any other drug to prevent early ovarian hyperstimulation syndrome (OHSS) with the exception of GnRH agonist for triggering of final follicular maturation, are not allowed.

During stimulation, subjects will be monitored by transvaginal ultrasound on stimulation days 1 and 5 and thereafter at least every second day. When the leading follicle reaches a diameter of ≥14 mm, transvaginal ultrasound will be performed daily. To prevent a premature luteinizing hormone (LH) surge, 250 μg GnRH antagonist (ganirelix acetate, GANIRELIX®, Merck Sharp & Dohme) will be initiated on stimulation day 5 for subjects with ≥3 follicles with a diameter of ≥10 mm. Subjects who fail to satisfy this GnRH antagonist criterion on stimulation day 5 will continue to be monitored at least every second day, and GnRH antagonist will be initiated when/if the criterion is met. The GnRH antagonist will be continued throughout the stimulation period. Triggering of final follicular maturation will be done as soon as ≥2 follicles with a diameter of ≥17 mm are observed. If there are <20 follicles with a diameter of ≥12 mm, 10,000 IU human chorionic gonadotropin (hCG; NOVAREL®, Ferring Pharmaceuticals) will be administered. If there are ≥20 follicles with a diameter of ≥12 mm or the serum estradiol concentration is 3,000 pg/mL (local laboratory), 4.0 mg GnRH agonist (leuprolide acetate, LEUPROLIDE ACETATE, Sandoz) will be administered, and the fresh blastocyst transfer will be cancelled. If after 8 days of stimulation, the investigator judges that the triggering criterion is not likely to be reached by day 20, the cycle will be cancelled. If the triggering criterion is not met after 20 days of stimulation, the cycle will be cancelled.

Oocyte retrieval will take place 36 h (±2 h) after triggering of final follicular maturation, and oocytes will be inseminated by IVF or ICSI 4 h (±1 h) after retrieval. Rescue ICSI is not allowed. Fertilization and embryo development will be assessed. For subjects who undergo triggering of final follicular maturation with hCG and have <20 oocytes retrieved, transfer will be performed on day 5 (blastocyst stage) after oocyte retrieval. All subjects will have transfer of one blastocyst of the highest quality available and remaining blastocysts will be cryopreserved by vitrification. For subjects with ≥20 oocytes retrieved following hCG administration and for subjects who undergo triggering of final follicular maturation with GnRH agonist, no transfer will take place in the fresh cycle and blastocysts will instead be cryopreserved.

A subject who fails to reach the triggering criterion due to poor ovarian response or who has ≤3 oocytes retrieved will be offered medication and financial support for an ART cycle with an approved gonadotropin preparation outside of the trial.

Vaginal progesterone inserts (progesterone, ENDOMETRIN®, Ferring Pharmaceuticals) 100 mg three times daily (TID) will be provided for luteal phase support from the day after oocyte retrieval and continuing until menses, negative β human chorionic gonadotropin (βhCG test), pregnancy loss or until ongoing pregnancy has been documented.

A serum βhCG test will be performed 10-14 days after transfer, clinical and vital pregnancy will be confirmed by transvaginal ultrasound 5-6 weeks after transfer, and ongoing pregnancy will be confirmed by transvaginal or abdominal ultrasound 8-9 weeks after transfer.

Cryopreserved Cycles

The trial covers cryopreserved cycles initiated within 12 months from the start of controlled ovarian stimulation. Either a programmed or natural cycle can be selected for any cryopreserved cycle.

Any programmed cryopreserved cycle will be initiated within 3 days of start of menses with administration of estradiol (ESTRADIOL Tablets USP, Teva Pharmaceuticals USA, Inc.) 2 mg TID or 3 mg two times daily (BID) (or 3 mg TID at the investigator's discretion, if a daily dose of 6 mg has been shown to be insufficient in a previous cycle). If after 10-12 days of estradiol treatment the endometrial thickness is ≥8 mm, the subject will initiate daily intramuscular (IM) injections of 50 mg progesterone (PROGESTERONE Injection USP, West-ward Pharmaceutical Corp or Watson Pharma, Inc.) within the next 5 days in conjunction with the estradiol treatment. The ultrasound evaluation can be repeated within 7 days if the endometrial thickness criterion is not met. In programmed cryopreserved cycles, transfer of one blastocyst of the highest quality available will occur on the 6th day from start of progesterone after warming and assessment of blastocyst survival and re-expansion. Luteal phase support (estradiol and IM progesterone) will continue to be administered until menses, negative βhCG test, pregnancy loss or until ongoing pregnancy has been documented.

Any natural cryopreserved cycle will be initiated 7 days after start of menses with monitoring of urinary LH on a daily basis by the subject. The day after confirmation of LH surge by serum LH (local laboratory) and endometrial thickness of ≥8 mm, the subject will start luteal phase support with vaginal progesterone inserts (progesterone, ENDOMETRIN, Ferring Pharmaceuticals) 100 mg TID. In a natural cryopreserved cycle, transfer of one blastocyst of the highest quality available will occur on day LH surge +7 after warming and assessment of blastocyst survival and re-expansion. Luteal phase support (vaginal progesterone) will continue to be administered until menses, negative βhCG test, pregnancy loss or until ongoing pregnancy has been documented.

Failure to achieve endometrial thickness ≥8 mm in the first cryopreserved cycle will result in cycle cancellation, and in the programmed cycles, administration of 100 mg IM progesterone (PROGESTERONE Injection USP, West-ward Pharmaceutical Corp or Watson Pharma, Inc.) to induce withdrawal bleeding. In subsequent cryopreserved cycles, blastocyst transfer can take place regardless of endometrial thickness at the investigator's discretion.

In both programmed and natural cryopreserved cycles, a serum βhCG test is performed 10-14 days after transfer, clinical and vital pregnancy will be confirmed by transvaginal ultrasound 5-6 weeks after transfer, and ongoing pregnancy will be confirmed by transvaginal or abdominal ultrasound 8-9 weeks after transfer.

After completion of the trial, the subject is allowed to use cryopreserved blastocysts in accordance with local guidelines and/or regulations.

All subjects with an ongoing pregnancy obtained in the fresh cycle or in cryopreserved cycles initiated within 12 months from the start of controlled ovarian stimulation will be followed until delivery to collect information on live birth rate. Furthermore, data will be collected on neonatal health, including minor/major congenital anomalies, at birth, 4 weeks and 1 year after birth.

Example 3—REKOVELLE®

REKOVELLE® is a recombinant FSH expressed in a PER.C6® cell line engineered by the methods disclosed in WO2013/020996 and WO2009/127826A. The Marketing Authorisation holder for REKOVELLE® is Ferring Pharmaceuticals NS of Kay Fiskers Plads 11, 2300 Copenhagen S, Denmark, and it is available in the UK from Ferring Pharmaceuticals of Drayton Hall, Church Road, West Drayton, UB7 7PS, UK. The active substance in REKOVELLE® is follitropin delta (FE999049). REKOVELLE® is highly sialylated and includes α2,3- and α2,6-sialylation, with about 85% to 90% of the total sialylation being α2,3-sialylation and about 10% to 15% of the total sialylation being α2,6-sialylation.

REKOVELLE® is a clear and colourless solution for injection. One millilitre of solution contains 33.3 micrograms of follitropin delta in each millilitre of solution. The other ingredients are phenol, polysorbate 20, L-methionine, sodium sulphate decahydrate, disodium phosphate dodecahydrate, concentrated phosphoric acid, sodium hydroxide and water for injections.

REFERENCES

Baenziger J U and Green E D. (1988). Pituitary glycoprotein hormone oligosaccharides: structure, synthesis and function of the asparagine-linked oligosaccharides on lutropin, follitropin and thyrotropin. Biochim Biophys Acta. 947 (2), 287-306.

Dalpathado D S, Irungu J, Go E P, Butnev V Y, Norton K, Bousfield G R, and Desaire H. (2006). Comparative glycomics of the glycoprotein follicle stimulating hormone: glycopeptide analysis of isolates from two mammalian species. Biochemistry. 45(28), 8665-8673.

Dewailly D, Andersen C Y, Balen A, Broekmans F, Dilaver N, Fanchin R, Griesinger G, Kelsey T W, La Marca A, Lambalk C et al. The physiology and clinical utility of anti-Mullerian hormone in women. Hum Reprod Update 2014; 20:370-385.

Dias J A, Van Roey P. (2001). Structural biology of human follitropin and its receptor. Arch Med Res. 32(6), 510-519

Fox K M, Dias J A, and Van Roey P. (2001). Three-dimensional structure of human follicle-stimulating hormone. Mol Endocrinol. 15(3), 378-89

Kagawa Y, Takasaki S, Utsumi J, Hosoi K, Shimizu H, Kochibe N, and Kobata A. (1988). Comparative study of the asparagine-linked sugar chains of natural human interferon-beta 1 and recombinant human interferon-beta 1 produced by three different mammalian cells. J Biol Chem. 263(33), 17508-17515.

Olivennes F, Howles C M, Borini A, Germond M, Trew G, Wikland M, Zegers-Hochschild F, Saunders H (2009) Individualizing FSH dose for assisted reproduction using a novel algorithm: the CONSORT study. Reprod Biomed Online. 2009 February; 18(2):195-204.

Pierce J G, and Parsons T F (1981) Glycoprotein hormones: structure and function Annu Rev Biochem. 50, 465-495.

Rathnam P, and Saxena B B. (1975). Primary amino acid sequence of follicle-stimulating hormone from human pituitary glands. I. alpha subunit. J Biol Chem.; 250(17): 6735-6746.

Ryan R J, Keutmann H T, Charlesworth M C, McCormick D J, Milius R P, Calvo F O and Vutyavanich T. (1987). Structure-function relationships of gonadotropins. Recent Prog Horm Res.; 43:383-429.

Saxena B B and Rathnam P. (1976) Amino acid sequence of the beta subunit of follicle-stimulating hormone from human pituitary glands. J Biol Chem. 251(4), 993-1005

Takeuchi M, Takasaki S, Miyazaki H, Kato T, Hoshi S, Kochibe N, and Kobata A (1988). Comparative study of the asparagine-linked sugar chains of human erythropoietins purified from urine and the culture medium of recombinant Chinese hamster ovary cells. J Biol Chem. 263(8), 3657-3663.

Ulloa-Aguirre A, Midgley A R Jr, Beitins I Z, and Padmanabhan V. (1995). Follicle-stimulating isohormones: characterization and physiological relevance. Endocr Rev. 16(6), 765-787.

Wide L, Naessén T, Sundström-Poromaa I, Eriksson K. (2007) Sulfonation and sialylation of gonadotropins in women during the menstrual cycle, after menopause, and with polycystic ovarian syndrome and in men. J Clin Endocrinol Metab.; 92(11), 4410-4417.

Yding Andersen C, Westergaard L G, and van Wely M. (2004). FSH isoform composition of commercial gonadotrophin preparations: a neglected aspect? Reprod Biomed Online. 9(2), 231-236.

There have been disclosed hereinbefore the compositions, compositions for use, uses and methods (e.g. methods of treatment) defined by the following numbered paragraphs:

1. A composition comprising recombinant follicle stimulating hormone (FSH) for use in the treatment of infertility in a patient of age≥35 years, wherein the composition is for administration at a (e.g. starting) dose of, or a (e.g. starting) dose equivalent to, 15 μg recombinant FSH per day.

2. A composition for use in the treatment of infertility in a patient of age≥35 years, wherein the composition comprises a (e.g. starting) dose of, or a (e.g. starting) dose equivalent to, 15 μg recombinant follicle stimulating hormone (FSH) per day.

3. A composition for use according to paragraph 1 or paragraph 2 wherein the composition is for administration at a (e.g. starting) dose of 15 μg recombinant FSH per day.

4. A composition comprising recombinant follicle stimulating hormone (FSH) for use in the treatment of infertility in a patient of age≥35 years, wherein the composition is for administration at a starting dose of 15 μg recombinant FSH per day, wherein the starting dose is administered on at least day 1 of treatment (preferably on at least day 1 and day 2 of treatment, more preferably on each of days 1 to 4 of treatment), optionally wherein the dose is (i) increased by a first incremental dose increase of 3 μg recombinant FSH on any subsequent day of treatment; and/or (ii) decreased by a first incremental dose decrease of 3 μg recombinant FSH on any subsequent day of treatment.

5. A composition for use according to paragraph 4 wherein the dose is maintained at the starting dose for the duration of the treatment.

6. A composition for use according to paragraph 4 wherein the first incremental dose increase of 3 μg recombinant FSH is (a) followed by at least one further incremental dose increase of 3 μg recombinant FSH at least two days after the previous incremental change in dose; and/or (b) followed by at least one incremental dose decrease of 3 μg recombinant FSH at least one day after the previous incremental change in dose.

7. A composition for use according to paragraph 4 wherein the first incremental dose decrease of 3 μg recombinant FSH is (a) followed by at least one incremental dose increase of 3 μg recombinant FSH at least two days after the previous incremental dose change in dose; and/or (b) followed by at least one further incremental dose decrease of 3 μg recombinant FSH at least one day after the previous change in dose.

8. A composition for use according to paragraph 4, 6 or 7 wherein the dose is increased to a maximum daily dose of 24 μg or decreased to a minimum daily dose of 6 μg.

9. A composition comprising recombinant follicle stimulating hormone (FSH) for use in the treatment of infertility in a patient identified as being of age≤34 years, wherein the composition is for administration at a (e.g. starting) dose of, or a (e.g. starting) dose equivalent to, 12 μg recombinant FSH per day.

10. A composition for use in the treatment of infertility in a patient identified as being of age≤34 years, wherein the composition comprises a (e.g. starting) dose of, or a (e.g. starting) dose equivalent to, 12 μg recombinant follicle stimulating hormone (FSH) per day.

11. A composition for use according to paragraph 9 or paragraph 10 wherein the composition is for administration at a (e.g. starting) dose of 12 μg recombinant FSH per day.

12. A composition comprising recombinant follicle stimulating hormone (FSH) for use in the treatment of infertility in a patient of age≤34 years, wherein the composition is for administration at a starting dose of 12 μg recombinant FSH per day, wherein the starting dose is administered on at least day 1 of treatment (preferably on at least day 1 and day 2 of treatment, more preferably on each of days 1 to 4 of treatment), optionally wherein the dose is
  (i) increased by a first incremental dose increase of 3 μg recombinant FSH on any subsequent day of treatment; and/or
  (ii) decreased by a first incremental dose decrease of 3 μg recombinant FSH on any subsequent day of treatment.

13. A composition for use according to paragraph 12 wherein the dose is maintained at the starting dose for the duration of the treatment.

14. A composition for use according to paragraph 12 wherein the first incremental dose increase of 3 μg recombinant FSH is (a) followed by at least one further incremental dose increase of 3 μg recombinant FSH at least two days after the previous incremental change in dose; and/or (b) followed by at least one incremental dose decrease of 3 μg recombinant FSH at least one day after the previous incremental change in dose.

15. A composition for use according to paragraph 12 wherein the first incremental dose decrease of 3 μg recombinant FSH is (a) followed by at least one incremental dose increase of 3 μg recombinant FSH at least two days after the previous incremental dose change in dose; and/or (b) followed by at least one further incremental dose decrease of 3 μg recombinant FSH at least one day after the previous change in dose.

16. A composition for use according to paragraph 12, 14 or 15 wherein the dose is increased to a maximum daily dose of 24 μg or decreased to a minimum daily dose of 6 μg.

17. A composition for use according to any of paragraphs 1 to 16 wherein the treatment of infertility comprises a step of determining the age of the patient, and a step of administering the defined dose of recombinant FSH to a patient having the defined age.

18. A composition for use according to any preceding paragraph wherein the recombinant FSH includes α2,6-sialylation and α2,3-sialylation, optionally wherein 1% to 50% of the total sialylation is α2, 6-sialyation, and 50% to 99% of the total sialylation is a 2,3-sialyation.

19. A composition for use according to any preceding paragraph wherein the patient is over 30 years of age and/or has previously failed at least one cycle of infertility treatment.

20. A composition for use according to any preceding paragraph wherein the treatment of infertility further comprises: retrieving (e.g. harvesting) oocyte(s); fertilizing (e.g. inseminating) the oocytes (s); and allowing the fertilized oocytes to develop to the blastocyst stage.

21. A composition for use according to paragraph 20 wherein the treatment of infertility further comprises assessing the quality of blastocysts obtained after fertilization of the harvested oocytes.

22. A composition for use according to any preceding paragraph wherein the treatment includes a step of monitoring the patient for over-response to treatment by identifying, during treatment, a patient with ≥20 follicles with a diameter of ≥12 mm and/or a serum estradiol concentration ≥3,000 pg/mL; and optionally administering a dose of GnRH agonist (e.g. 4.0 mg) to the patient identified during treatment as having ≥20 follicles with a diameter of 12 mm and/or a serum estradiol concentration ≥3,000 pg/mL.

23. A composition for use according to any preceding paragraph wherein the treatment of infertility is for development of multiple follicles and pregnancy after fresh and/or cryopreserved embryo transfer in ovulatory women undergoing assisted reproductive technology (ART).

24. A composition for use according to any preceding paragraph wherein the treatment of infertility is for optimising cumulative efficiency and/or reducing ovarian hyper-stimulation syndrome (OHSS) risk.

25. A method of treating infertility in a female patient age≥35 years, comprising administering recombinant follicle stimulating hormone (rFSH) at a dose of, or a dose equivalent to, 15 μg rFSH per day starting on day 1 of treatment.

26. The method of paragraph 25, wherein the rFSH is administered at a dose of 15 μg rFSH per day starting on day 1 of treatment.

27. The method of paragraph 25, wherein the method comprises:
administering rFSH at a starting dose of 15 μg per day for at least 1-4 days,
optionally, on any subsequent day, (i) increasing the dose of rFSH by an incremental dose increase of 3 μg rFSH or (ii) decreasing the dose of rFSH by an incremental dose decrease of 3 μg rFSH.

28. The method of paragraph 27, wherein the rFSH dose is maintained at the starting dose of 15 μg per day throughout the treatment.

29. The method of paragraph 27, wherein an incremental dose increase of 3 μg rFSH is followed by (a) a further incremental dose increase of 3 μg rFSH at least two days after the previous incremental dose increase or (b) an incremental dose decrease of 3 μg rFSH at least one day after the previous incremental dose increase.

30. The method of paragraph 27, wherein an incremental dose decrease of 3 μg rFSH is followed by (a) an incremental dose increase of 3 μg rFSH at least two days after the previous incremental dose decrease or (b) a further incremental dose decrease of 3 μg rFSH at least one day after the previous incremental dose decrease.

31. The method of paragraph 27, wherein, throughout the treatment, the maximum daily dose of rFSH is 24 μg and the minimum daily dose is 6 μg.

32. The method of paragraph 25, wherein the rFSH includes α2,6-sialylation and α2,3-sialylation.

33. The method of paragraph 32, wherein 1% to 50% of the total sialylation is α2, 6-sialyation, and 50% to 99% of the total sialylation is a 2,3-sialyation.

34. The method of paragraph 32, wherein 5% to 20% of the total sialylation is α2, 6-sialyation, and 80% to 95% of the total sialylation is 2,3-sialyation.

35. The method of paragraph 32, wherein 50% to 80% of the total sialylation is α2, 6-sialyation, and 20% to 50% of the total sialylation is 2,3-sialylation.

36. The method of paragraph 25, further comprising, prior to administering the rFSH, determining the age of the patient.

37. The method of paragraph 25, further comprising: retrieving oocyte(s); fertilizing oocyte(s); allowing fertilized oocyte(s) to develop to the blastocyst stage, and, optionally, assessing the quality of the blastocyst(s).

38. The method of paragraph 25, further comprising monitoring the patient for over-response to treatment, and, optionally administering a dose of GnRH agonist to a patient identified as having ≥20 follicles with a diameter of ≥12 mm and/or a serum estradiol concentration ≥3,000 pg/mL.

39. The method of paragraph 25, wherein the patient has previously failed at least one cycle of infertility treatment.

40. The method of paragraph 25, wherein the method is effective for optimising cumulative efficiency and/or reducing OHSS risk.

41. The method of paragraph 25, wherein the treatment of infertility is for development of multiple follicles and pregnancy after fresh and/or cryopreserved embryo transfer in ovulatory women undergoing assisted reproductive technology (ART).

42. A method of treating infertility in a female patient identified as being of ages≤34 years, comprising administering recombinant follicle stimulating hormone (rFSH) at a dose of, or a dose equivalent to, 12 μg rFSH per day starting on day 1 of treatment.

43. The method of paragraph 42, wherein the rFSH is administered at a dose of 12 μg rFSH per day starting on day 1 of treatment.

44. The method of paragraph 42, wherein the method comprises:
administering rFSH at a starting dose of 12 μg per day for at least 1-4 days,
optionally, on any subsequent day, (i) increasing the dose of rFSH by an incremental dose increase of 3 μg rFSH or (ii) decreasing the dose of rFSH by an incremental dose decrease of 3 μg rFSH.

45. The method of paragraph 44, wherein the rFSH dose is maintained at the starting dose of 12 μg per day throughout the treatment.

46. The method of paragraph 44, wherein an incremental dose increase of 3 μg rFSH is followed by (a) a further incremental dose increase of 3 μg rFSH at least two days after the previous incremental dose increase or (b) an incremental dose decrease of 3 μg rFSH at least one day after the previous incremental dose increase.

47. The method of paragraph 44, wherein an incremental dose decrease of 3 μg rFSH is followed by (a) an incremental dose increase of 3 μg rFSH at least two days after the previous incremental dose decrease or (b) a further incremental dose decrease of 3 μg rFSH at least one day after the previous incremental dose decrease.

48. The method of paragraph 44 wherein, throughout the treatment, the maximum daily dose of rFSH is 24 μg and the minimum daily dose is 6 μg.

49. The method of paragraph 42, wherein the rFSH includes α2,6-sialylation and α2,3-sialylation.

50. The method of paragraph 49, wherein the rFSH includes α2,6-sialylation and α2,3-sialylation, wherein 1% to 50% of the total sialylation is α2, 6-sialyation, and 50% to 99% of the total sialylation is a 2,3-sialyation.

51. The method of paragraph 49, wherein 5% to 20% of the total sialylation is α2, 6-sialyation, and 80% to 95% of the total sialylation is 2,3-sialyation.

52. The method of paragraph 49, wherein 50% to 80% of the total sialylation is α2, 6-sialyation, and 20% to 50% of the total sialylation is 2,3-sialyation.

53. The method of paragraph 42, further comprising, prior to administering the rFSH, determining the age of the patient.

54. The method of paragraph 42, further comprising: retrieving oocyte(s); fertilizing oocyte(s); allowing fertilized oocyte(s) to develop to the blastocyst stage, and, optionally, assessing the quality of the blastocyst(s).

55. The method of paragraph 42, further comprising monitoring the patient for over-response to treatment, and, optionally administering a dose of GnRH agonist to a patient identified as having ≥20 follicles with a diameter of ≥12 mm and/or a serum estradiol concentration ≥3,000 pg/mL.

56. The method of paragraph 42, wherein the patient is over 30 years of age and/or has previously failed at least one cycle of infertility treatment.

57. The method of paragraph 42, wherein the method is effective for optimising cumulative efficiency and/or reducing OHSS risk.

58. The method of paragraph 42, wherein the treatment of infertility is for development of multiple follicles and pregnancy after fresh and/or cryopreserved embryo transfer in ovulatory women undergoing assisted reproductive technology (ART).

59. A method of treating infertility in a female patient, comprising:
  determining the age of the patient;
  if the patient is age≥35 years, administering recombinant follicle stimulating hormone (rFSH) at a starting dose of 15 μg rFSH per day for at least 1-4 days;
  if the patient is ages≤34 years, administering recombinant follicle stimulating hormone (rFSH) at a starting dose of 12 μg rFSH per day for at least 1-4 days;
  optionally, on any subsequent day, (i) increasing the dose of rFSH by an incremental dose increase of 3 μg rFSH or (ii) decreasing the dose of rFSH by an incremental dose decrease of 3 μg rFSH,
  wherein, throughout the treatment, the maximum daily dose of rFSH is 24 μg and the minimum daily dose is 6 μg.

The invention claimed is:

1. A method of treating infertility in a female patient ≥35 years of age, comprising selecting a female patient ≥35 years of age and subcutaneously administering to the patient recombinant follicle stimulating hormone (rFSH) at a starting dose of 15 μg rFSH per day from day 1 of treatment, wherein the rFSH contains both α2,3- and α2,6-linked sialic acid, wherein the rFSH has a total sialylation comprised of 5% to 20% α2,6-sialyation and 80% to 95% α2,3-sialylation.

2. The method of claim 1, wherein the method comprises administering rFSH at the starting dose of 15 μg per day for at least 4 days.

3. The method of claim 1, wherein the rFSH dose is maintained at the starting dose of 15 μg per day throughout the treatment.

4. The method of claim 1, wherein the rFSH is administered in a composition in which the rFSH is the sole active pharmaceutical ingredient.

5. The method of claim 1, wherein the patient has previously failed at least one cycle of infertility treatment.

6. A method of selecting a starting dose of recombinant follicle stimulating hormone (rFSH) for the treatment of infertility in a female patient, comprising:
  determining the age of the patient and, if the patient's age is ≥35 years, selecting a starting dose of 15 μg rFSH per day, wherein the starting dose is selected independent of the patient's serum anti-Mullerian hormone (AMH) concentration, and
  administering the selected starting dose of 15 μg rFSH per day to the patient by subcutaneous injection, wherein the rFSH contains both α2,3- and α2,6-linked sialic acid, wherein the rFSH has a total sialylation comprised of 5% to 20% α2,6-sialyation and 80% to 95% α2,3-sialylation.

* * * * *